United States Patent
Reubelt et al.

(10) Patent No.: US 9,474,619 B2
(45) Date of Patent: Oct. 25, 2016

(54) GLENOID COMPONENT WITH IMPROVED FIXATION STABILITY

(75) Inventors: Leo M. Reubelt, Hawthorne, NJ (US); Peter L. Verrillo, Wood Ridge, NJ (US)

(73) Assignee: Tornier, Inc., Bloomington, MN (US)

( * ) Notice: Subject to any disclaimer, the term of this patent is extended or adjusted under 35 U.S.C. 154(b) by 2073 days.

(21) Appl. No.: 11/689,424

(22) Filed: Mar. 21, 2007

(65) Prior Publication Data

US 2007/0225817 A1  Sep. 27, 2007

Related U.S. Application Data

(60) Provisional application No. 60/784,237, filed on Mar. 21, 2006.

(51) Int. Cl.
*A61F 2/40* (2006.01)
*A61F 2/30* (2006.01)
*A61F 2/46* (2006.01)

(52) U.S. Cl.
CPC .... *A61F 2/4081* (2013.01); *A61F 2002/30878* (2013.01); *A61F 2002/30884* (2013.01); *A61F 2002/30892* (2013.01); *A61F 2002/30897* (2013.01); *A61F 2002/30934* (2013.01);
(Continued)

(58) Field of Classification Search
CPC .................. A61F 2/4081; A61F 2002/30878; A61F 2/30897
USPC ............................................ 623/19.11–19.13
See application file for complete search history.

(56) References Cited

U.S. PATENT DOCUMENTS

| 3,694,820 A | 10/1972 | Scales et al. |
| 3,815,157 A | 6/1974 | Skorecki et al. |

(Continued)

FOREIGN PATENT DOCUMENTS

| CH | 426096 | 12/1966 |
| CH | 507704 | 5/1971 |

(Continued)

OTHER PUBLICATIONS

Boileau et al., U.S. Appl. No. 12/020,913, entitled "Method and Apparatus for Fitting a Shoulder Prosthesis" filed Jan. 28, 2008.
(Continued)

*Primary Examiner* — Bruce E Snow
*Assistant Examiner* — Melissa Hoban
(74) *Attorney, Agent, or Firm* — Knobbe Martens Olson & Bear LLP

(57) ABSTRACT

A glenoid component is provided to reduce glenoid loosening when implanted in orthopedic joint replacement/reconstruction, such for a shoulder. The glenoid component can include pegs or a keel and articulating surface geometry that uses complex, non-spherical geometry to recreate a level of constraint that is adequate, but not excessive, to thereby mitigate loosening of the glenoid component after implantation. In addition, some embodiments provide that peak stresses both within cement and at an interface of the cement and a supportive component can be reduced. Further, geometry of the pegs can allow stresses to be evenly applied to a cement mantle formed in the supportive component. Finally, the pegs can be configured to desired lengths in order to avoid placement in areas of the supportive component, for example, that have insufficient bone stock.

20 Claims, 12 Drawing Sheets

(52) U.S. Cl.
  CPC ............... A61F2002/30935 (2013.01); A61F
  2002/4631 (2013.01)

(56) References Cited

U.S. PATENT DOCUMENTS

| | | | |
|---|---|---|---|
| 3,842,442 A | 10/1974 | Kolbel | |
| 3,864,758 A | 2/1975 | Yakich | |
| 3,869,730 A | 3/1975 | Skobel | |
| 3,916,451 A | 11/1975 | Buechel et al. | |
| 3,978,528 A | 9/1976 | Crep | |
| 3,979,778 A | 9/1976 | Stroot | |
| 3,987,500 A * | 10/1976 | Schlein | 623/21.18 |
| 3,992,726 A | 11/1976 | Freeman et al. | |
| 4,003,095 A | 1/1977 | Gristina | |
| 4,030,143 A | 6/1977 | Elloy et al. | |
| 4,040,131 A | 8/1977 | Gristina | |
| 4,054,955 A | 10/1977 | Seppo | |
| 4,135,517 A | 1/1979 | Reale | |
| 4,179,758 A | 12/1979 | Gristina | |
| 4,206,517 A | 6/1980 | Pappas et al. | |
| 4,261,062 A | 4/1981 | Amstutz et al. | |
| 4,550,450 A | 11/1985 | Kinnett | |
| 4,693,723 A | 9/1987 | Gabard | |
| 4,822,370 A | 4/1989 | Schelhas | |
| 4,846,840 A | 7/1989 | Leclercq et al. | |
| 4,865,605 A | 9/1989 | Dines et al. | |
| 4,865,609 A | 9/1989 | Roche | |
| 4,892,549 A | 1/1990 | Figgie, III et al. | |
| 4,919,670 A | 4/1990 | Dale et al. | |
| 4,957,510 A | 9/1990 | Cremascoli | |
| 4,963,155 A | 10/1990 | Lazerri et al. | |
| 5,032,132 A | 7/1991 | Matsen, III et al. | |
| 5,080,673 A | 1/1992 | Burkhead et al. | |
| 5,080,674 A * | 1/1992 | Jacobs et al. | 623/20.17 |
| 5,080,685 A | 1/1992 | Bolesky et al. | |
| 5,127,920 A | 7/1992 | MacArthur | |
| 5,135,529 A | 8/1992 | Paxson et al. | |
| 5,163,961 A | 11/1992 | Harwin | |
| 5,181,928 A | 1/1993 | Bolesky et al. | |
| 5,192,329 A | 3/1993 | Christie et al. | |
| 5,201,882 A | 4/1993 | Paxson | |
| 5,206,925 A | 4/1993 | Nakazawa et al. | |
| 5,222,984 A | 6/1993 | Forte | |
| 5,261,914 A | 11/1993 | Warren | |
| 5,314,479 A | 5/1994 | Rockwood, Jr. et al. | |
| 5,314,487 A | 5/1994 | Schryver et al. | |
| 5,330,531 A | 7/1994 | Cappana | |
| 5,358,526 A | 10/1994 | Tornier | |
| 5,383,936 A | 1/1995 | Kubein-Meesenburg et al. | |
| 5,425,779 A | 6/1995 | Schlosser | |
| 5,443,519 A | 8/1995 | Averill et al. | |
| 5,462,563 A | 10/1995 | Shearer et al. | |
| 5,507,817 A | 4/1996 | Craig et al. | |
| 5,507,818 A | 4/1996 | McLaughlin | |
| 5,507,824 A | 4/1996 | Lennox | |
| 5,549,682 A | 8/1996 | Roy | |
| 5,580,352 A | 12/1996 | Sekel | |
| 5,702,447 A | 12/1997 | Walch et al. | |
| 5,702,457 A | 12/1997 | Walch et al. | |
| 5,702,486 A | 12/1997 | Craig et al. | |
| 5,723,018 A | 3/1998 | Cyprien et al. | |
| 5,728,161 A | 3/1998 | Camino et al. | |
| 5,741,335 A | 4/1998 | Gerber et al. | |
| 5,755,807 A | 5/1998 | Anstaett et al. | |
| 5,800,551 A | 9/1998 | Williamson et al. | |
| 5,879,405 A | 3/1999 | Ries et al. | |
| 5,902,340 A | 5/1999 | White et al. | |
| 5,910,171 A | 6/1999 | Kummer et al. | |
| 5,928,285 A | 7/1999 | Bigliani et al. | |
| 5,944,758 A | 8/1999 | Mansat et al. | |
| 5,961,555 A | 10/1999 | Huebner | |
| 5,984,927 A | 11/1999 | Wenstrom, Jr. et al. | |
| 6,015,437 A | 1/2000 | Stossel | |
| 6,033,439 A | 3/2000 | Camino et al. | |
| 6,045,582 A | 4/2000 | Prybyla | |
| 6,045,583 A | 4/2000 | Gross et al. | |
| 6,102,953 A | 8/2000 | Huebner | |
| 6,129,764 A | 10/2000 | Servidio | |
| 6,165,224 A | 12/2000 | Tornier | |
| 6,171,341 B1 | 1/2001 | Boileau et al. | |
| 6,197,062 B1 | 3/2001 | Fenlin | |
| 6,197,063 B1 | 3/2001 | Dews | |
| 6,203,575 B1 | 3/2001 | Farey | |
| 6,206,925 B1 | 3/2001 | Tornier | |
| 6,228,120 B1 | 5/2001 | Leonard et al. | |
| 6,267,767 B1 | 7/2001 | Strobel et al. | |
| 6,283,999 B1 | 9/2001 | Rockwood, Jr. | |
| 6,312,467 B1 | 11/2001 | McGee | |
| 6,334,874 B1 | 1/2002 | Tornier et al. | |
| 6,364,910 B1 | 4/2002 | Schultz et al. | |
| 6,368,352 B1 | 4/2002 | Camino et al. | |
| 6,368,353 B1 | 4/2002 | Arcand | |
| 6,398,812 B1 | 6/2002 | Masini | |
| 6,406,495 B1 | 6/2002 | Schoch | |
| 6,406,496 B1 | 6/2002 | Rüter | |
| 6,436,144 B1 | 8/2002 | Ahrens | |
| 6,436,147 B1 | 8/2002 | Zweymuller | |
| 6,458,136 B1 | 10/2002 | Allard et al. | |
| 6,475,243 B1 | 11/2002 | Sheldon et al. | |
| 6,494,913 B1 | 12/2002 | Huebner | |
| 6,506,214 B1 | 1/2003 | Gross | |
| 6,508,840 B1 | 1/2003 | Rockwood, Jr. et al. | |
| 6,514,287 B2 | 2/2003 | Ondrla et al. | |
| 6,520,994 B2 | 2/2003 | Nogarin | |
| 6,530,957 B1 | 3/2003 | Jack | |
| 6,558,425 B2 | 5/2003 | Rockwood | |
| 6,569,202 B2 | 5/2003 | Whiteside | |
| 6,620,197 B2 | 9/2003 | Maroney et al. | |
| 6,626,946 B1 | 9/2003 | Walch et al. | |
| 6,673,114 B2 | 1/2004 | Hartdegen et al. | |
| 6,673,115 B2 | 1/2004 | Resch et al. | |
| 6,679,916 B1 | 1/2004 | Frankle et al. | |
| 6,736,851 B2 | 5/2004 | Maroney et al. | |
| 6,746,487 B2 | 6/2004 | Scifert et al. | |
| 6,749,637 B1 | 6/2004 | Bahler | |
| 6,755,866 B2 | 6/2004 | Southworth | |
| 6,761,740 B2 | 7/2004 | Tornier | |
| 6,780,190 B2 | 8/2004 | Maroney | |
| 6,783,549 B1 | 8/2004 | Stone et al. | |
| 6,790,234 B1 | 9/2004 | Frankle | |
| 6,863,690 B2 | 3/2005 | Ball et al. | |
| 6,875,234 B2 | 4/2005 | Lipman et al. | |
| 6,887,277 B2 | 5/2005 | Rauscher et al. | |
| 6,890,358 B2 | 5/2005 | Ball et al. | |
| 6,942,699 B2 | 9/2005 | Stone et al. | |
| 6,953,478 B2 | 10/2005 | Bouttens et al. | |
| 6,969,406 B2 | 11/2005 | Tornier | |
| 7,011,686 B2 | 3/2006 | Ball et al. | |
| 7,033,396 B2 | 4/2006 | Tornier | |
| 7,066,959 B2 | 6/2006 | Errico | |
| 7,108,719 B2 | 9/2006 | Horber | |
| 7,166,132 B2 | 1/2007 | Callaway et al. | |
| 7,169,184 B2 | 1/2007 | Dalla Pria | |
| 7,175,663 B1 | 2/2007 | Stone | |
| 7,195,645 B2 | 3/2007 | Disilvestro et al. | |
| 7,238,207 B2 | 7/2007 | Blatter et al. | |
| 7,238,208 B2 | 7/2007 | Camino et al. | |
| 7,297,163 B2 | 11/2007 | Huebner | |
| 7,309,360 B2 | 12/2007 | Tornier et al. | |
| 7,320,709 B2 * | 1/2008 | Felt et al. | 623/20.16 |
| 7,329,284 B2 | 2/2008 | Maroney et al. | |
| 7,338,498 B2 | 3/2008 | Long et al. | |
| 7,338,528 B2 | 3/2008 | Stone et al. | |
| 2001/0032021 A1 | 10/2001 | McKinnon | |
| 2001/0047210 A1 | 11/2001 | Wolf | |
| 2001/0049561 A1 | 12/2001 | Dews et al. | |
| 2002/0032484 A1 | 3/2002 | Hyde, Jr. | |
| 2002/0082702 A1 | 6/2002 | Resch et al. | |
| 2002/0095214 A1 | 7/2002 | Hyde, Jr. | |
| 2002/0099381 A1 | 7/2002 | Maroney | |
| 2002/0138148 A1 | 9/2002 | Hyde, Jr. | |
| 2002/0143402 A1 | 10/2002 | Steinberg | |
| 2002/0151982 A1 | 10/2002 | Masini | |
| 2003/0009171 A1 | 1/2003 | Tornier | |

(56) References Cited

U.S. PATENT DOCUMENTS

| | | | |
|---|---|---|---|
| 2003/0060885 A1* | 3/2003 | Fell et al. | 623/14.12 |
| 2004/0006392 A1 | 1/2004 | Grusin et al. | |
| 2004/0006393 A1* | 1/2004 | Burkinshaw | 623/20.3 |
| 2004/0034431 A1 | 2/2004 | Maroney et al. | |
| 2004/0122520 A1 | 6/2004 | Lipman et al. | |
| 2004/0133276 A1 | 7/2004 | Lang et al. | |
| 2004/0138754 A1 | 7/2004 | Lang et al. | |
| 2004/0148033 A1 | 7/2004 | Schroeder | |
| 2004/0193276 A1 | 9/2004 | Maroney et al. | |
| 2004/0193277 A1 | 9/2004 | Long et al. | |
| 2004/0193278 A1 | 9/2004 | Maroney et al. | |
| 2004/0210317 A1 | 10/2004 | Maroney et al. | |
| 2004/0220674 A1 | 11/2004 | Pria | |
| 2004/0225367 A1 | 11/2004 | Glien et al. | |
| 2004/0230197 A1 | 11/2004 | Tornier et al. | |
| 2004/0267370 A1 | 12/2004 | Ondria | |
| 2005/0008672 A1 | 1/2005 | Winterbottom et al. | |
| 2005/0015154 A1 | 1/2005 | Lindsey et al. | |
| 2005/0043805 A1 | 2/2005 | Chudik | |
| 2005/0049709 A1 | 3/2005 | Tornier | |
| 2005/0065612 A1 | 3/2005 | Winslow | |
| 2005/0085919 A1 | 4/2005 | Durand-Allen et al. | |
| 2005/0085921 A1 | 4/2005 | Gupta et al. | |
| 2005/0090902 A1 | 4/2005 | Masini | |
| 2005/0107882 A1 | 5/2005 | Stone et al. | |
| 2005/0113931 A1 | 5/2005 | Horber | |
| 2005/0119531 A1 | 6/2005 | Sharratt | |
| 2005/0143829 A1 | 6/2005 | Ondria et al. | |
| 2005/0165490 A1 | 7/2005 | Tornier | |
| 2005/0177241 A1 | 8/2005 | Angibaud et al. | |
| 2005/0197708 A1 | 9/2005 | Stone et al. | |
| 2005/0203631 A1* | 9/2005 | Daniels et al. | 623/20.32 |
| 2005/0209700 A1 | 9/2005 | Rockwood et al. | |
| 2005/0216092 A1 | 9/2005 | Marik et al. | |
| 2005/0251263 A1 | 11/2005 | Forrer et al. | |
| 2005/0256584 A1 | 11/2005 | Farrar | |
| 2005/0267590 A1 | 12/2005 | Lee | |
| 2005/0278030 A1 | 12/2005 | Tornier et al. | |
| 2005/0278032 A1 | 12/2005 | Tornier et al. | |
| 2005/0278033 A1 | 12/2005 | Tornier et al. | |
| 2005/0288681 A1 | 12/2005 | Klotz et al. | |
| 2005/0288791 A1 | 12/2005 | Tornier et al. | |
| 2006/0004462 A1 | 1/2006 | Gupta | |
| 2006/0009852 A1 | 1/2006 | Winslow et al. | |
| 2006/0020344 A1 | 1/2006 | Schultz et al. | |
| 2006/0030946 A1 | 2/2006 | Ball et al. | |
| 2006/0111787 A1* | 5/2006 | Bailie et al. | 623/19.13 |
| 2006/0241775 A1 | 10/2006 | Buss | |
| 2007/0225818 A1 | 9/2007 | Reubelt et al. | |
| 2007/0225821 A1 | 9/2007 | Reubelt et al. | |
| 2007/0244564 A1 | 10/2007 | Ferrand et al. | |
| 2007/0250174 A1 | 10/2007 | Tornier et al. | |

FOREIGN PATENT DOCUMENTS

| | | |
|---|---|---|
| DE | 19509037 | 9/1996 |
| DE | 19630298 | 1/1998 |
| EP | 0257359 | 3/1988 |
| EP | 0299889 | 1/1989 |
| EP | 0524857 | 1/1993 |
| EP | 0549480 | 6/1993 |
| EP | 0599429 | 6/1994 |
| EP | 0617934 | 10/1994 |
| EP | 0664108 | 7/1995 |
| EP | 0679375 | 11/1995 |
| EP | 0712617 | 5/1996 |
| EP | 0715836 | 6/1996 |
| EP | 0797694 | 10/1997 |
| EP | 0807426 | 11/1997 |
| EP | 0809986 | 12/1997 |
| EP | 0864306 | 9/1998 |
| EP | 0903127 | 3/1999 |
| EP | 0903128 | 3/1999 |
| EP | 0927548 | 7/1999 |
| EP | 1062923 | 12/2000 |
| EP | 1064890 | 1/2001 |
| EP | 1195149 | 4/2002 |
| EP | 1380274 | 1/2004 |
| EP | 1402854 | 3/2004 |
| FR | 2248820 | 5/1975 |
| FR | 2545352 | 11/1984 |
| FR | 2574283 | 6/1986 |
| FR | 2652498 | 4/1991 |
| FR | 2664809 | 1/1992 |
| FR | 2699400 | 6/1994 |
| FR | 2721200 | 12/1995 |
| FR | 2726994 | 5/1996 |
| FR | 2737107 | 1/1997 |
| FR | 2835425 | 8/2003 |
| FR | 2836039 | 8/2003 |
| SU | 749392 | 7/1980 |
| WO | WO 91/07932 | 6/1991 |
| WO | WO 93/09733 | 5/1993 |
| WO | WO 96/17553 | 6/1996 |
| WO | WO 98/46172 | 10/1998 |
| WO | WO 99/49792 | 10/1999 |
| WO | WO 99/65413 | 12/1999 |
| WO | WO 00/15154 | 3/2000 |
| WO | WO 00/41653 | 7/2000 |
| WO | WO 01/47442 | 7/2001 |
| WO | WO 02/39931 | 5/2002 |
| WO | WO 02/39933 | 5/2002 |
| WO | WO 02/067821 | 9/2002 |
| WO | WO 03/005933 | 1/2003 |
| WO | WO03/094806 | 11/2003 |
| WO | WO 2007/109319 | 2/2007 |
| WO | WO 2007/109291 | 9/2007 |
| WO | WO 2007/109340 | 9/2007 |

OTHER PUBLICATIONS

John M. Fenlin Jr., M.D., Symposium on Surgery of the Shoulder, "Total Glenohumeral Joint Replacement," *Orthopedic Clinics of North America*, vol. 6, No. 2, Apr. 1975, pp. 565-583.
"Aequalis-Fracture Suture Technique in 5 Steps," Tornier, Inc.
"Aequalis-Fracture Shoulder Prosthesis—Surgical Technique," Tornier, Inc.
"Aequalis® Press-Fit Shoulder Prosthesis—Surgical Technique," Tornier, Inc.
Bigliani/Flatow®—The Complete Shoulder Solution, 4-Part Fracture of the Humerus Surgical Technique, Zimmer, Inc., 2000.
"Bio-Modular®/ Bi-Polar Shoulder Arthroplasty," Biomet, Inc., 1997.
"Bio-Modular® Choice, Shoulder System," Biomet Orthopedics, Inc., 2004.
"Bio-Modular Total Shoulder Surgical Technique," Biomet Orthopedics, Inc., 2001.
"Copeland™ Humeral Resurfacing Head," Biomet Orthopedics, Inc., 2001.
"Global C.A.P.™ Surgical technique, resurfacing humeral head implant," DePuy International, Ltd., 2004.
Boileau, et al. "Adaptability and modularity of shoulder prosthese," *Maitrise Orthopédique*, https://www.maitriseorthop.com/corpusmaitri/orthopaedic/prothese_epaule_orthop/boileau_us.shtml, Jan. 3, 2006.
Boileau, et al. "Arthroscopic Repair of Full-Thickness Tears of the Supraspinatus: Does the tendon really heal?," *The Journal of Bone and Joint Surgery, Inc.*, pp. 1229-1240, 2005.
"Design Rationale," Latitude®.
Klein, Travis J., et al. "Mechanically favorable bone remodeling in rotator cuff arthropathy patients with good function," Minneapolis Sports Medicine Center and University of Minnesota.
Mansat, Michel, "Neer 3™, Surgical Technique for Fractrures," Smith & Nephew, 2000.
Mole, M.D., et al., "Aequalis-Reversed™ Shoulder Prosthesis, Surgical Technique," Tornier, Inc.
"Offset Head, Bio-Modular® Total Shoulder," Biomet, Inc. 2000.
"The Foundation® Total Shoulder System," Encore Surgical.
"The Townley Modular Shoulder, Design by Reason," Biopro, Inc.

(56) References Cited

OTHER PUBLICATIONS

"Delta CTA™ Reverse Shoulder Prosthesis," DePuy International, Ltd., 2004.
Beuchel M.D., Frederick F. "Beuchel-Pappas™ Modular Salvage Shoulder System," Endotec, Inc., 2000.
Beuchel M.D., Frederick F. "Beuchel-Pappas™ Resurfacing Shoulder System," Endotec, Inc., 2000.
Apoil, André "A Condyle for the Rotator Cuff Muscles, the total shoulder prosthesis," Aesculap®, 1994.
International Search Report and Written Opinion from related International Patent Application No. PCT/US07/07018 dated Feb. 20, 2008.
"Tornier Surgical Technique Addendum, Tornier Aequalis® Reversed Hemi-Adaptor Technique," Tornier, Inc., Aug. 8, 2005.
"Tornier Surgical Technique Addendum, Aequalis® Reversed Shoulder Polyethylene Insert," Tornier, Inc., Aug. 8, 2005.
"Anatomic Glenoid, Surgical Technique," Smith & Nephew, 2000.
"Anatomical Shoulder™ Cemented Shoulder Prosthesis Product Information and Surgical Technique," Sulzer Medica, 2000.
"Anatomical Shoulder™ System Surgical Technique—Removable head option for improved surgical results," Zimmer, Inc., 2004.
"Anatomical Shoulder™ System—The new removable head option," Zimmer, Inc., 2004.
"Aequalis®—Glenoid Keeled and Pegged—Surgical Technique," Tornier, Inc.
"Bigliani/ Flatow®—The Complete Shoulder Solution, Designed by Shoulder Surgeons for Shoulder Surgery," Zimmer, Inc., 2001.
Beuchel M.D., Frederick F. "Beuchel-Pappas™ Total Shoulder System," Endotec, Inc., 2000.
Cofield, M.D., Robert H. "Cofield Total Shoulder System, Surgical Technique," Smith & Nephew, 1997.
Hertel M.D., PD, Ralph. "Technical considerations for implantation of EPOCA glenoid components (Leseprobe)," *Epoca Newsletter*, May 14, 2001.
Nicholson, Gregory P., "Arthroplasty and Rotator Cuff Deficiency," Chapter 7, pp. 149-166.
"Tornier Aequalis® Reversed 2 Prong Capsular Retractor," Tornier, Inc., Oct. 8, 2005.
"Tornier Aequalis® Reversed Shoulder G2 Baseplate," Tornier, Inc., Oct. 8, 2005.
"Zimmer® Bigliani/ Flatow®—The Complete Shoulder Solution, Total Shoulder Arthroplasty Surgical Technique," Zimmer, Inc., 2003.
"Zimmer® Shoulder Retractors," Zimmer, Inc., 2000.

\* cited by examiner

GLENOID COMPONENT WITH IMPROVED FIXATION STABILITY

CROSS-REFERENCE TO RELATED APPLICATIONS

The present application is based on and claims priority under 35 U.S.C. §120 to U.S. Provisional Application No. 60/784,237, filed on Mar. 21, 2007, entitled "GLENOID COMPONENT WITH IMPROVED FIXATION STABILITY," the entire contents of which is expressly incorporated by reference herein.

BACKGROUND

1. Field of the Inventions

The present inventions relate generally to orthopedic joint replacements, and more specifically, to a glenoid component.

2. Description of the Related Art

Anatomically, a joint is a more or less movable junction in the body of a subject of two or more bones. As used herein, the term is meant to include the different kinds of ligaments, tendons, cartilages, bursae, synovial membranes and bones comprising the mobile skeletal system of a subject in various quantities and configurations.

The shoulder joint is the body's most mobile joint, in that it can turn in many directions. The shoulder is a ball-and-socket joint made up of three bones: the upper arm bone (humerus), shoulder blade (scapula) and collarbone (clavicle). Two joints facilitate shoulder movement. The acromioclavicular (AC) joint joins one end of the collarbone with the shoulder blade; it is located between the acromion (the part of the scapula that forms the highest point of the shoulder) and the clavicle. The other end of the collarbone is joined with the breastbone (sternum) by the sternoclavicular joint. The glenohumeral joint, commonly called the shoulder joint, is a ball-and-socket type joint that helps move the shoulder forward and backward and allows the arm to rotate in a circular fashion or hinge out and up away from the body. The ball of the glenohumeral joint is the top, rounded portion of the humerus; the socket, or glenoid, is a dish-shaped part of the outer edge of the scapula into which the ball fits. The socket of the glenoid is surrounded by a soft-tissue ring of fibrocartilage (the glenoid labrum) that runs around the cavity of the scapula (glenoid cavity) in which the head of the humerus fits. The labrum deepens the glenoid cavity and effectively increases the surface of the shoulder joint, which helps stabilize the joint.

The bones of the shoulder are held in place by muscles, tendons (tough cords of tissue that attach the shoulder muscles to bone and assist the muscles in moving the shoulder) and ligaments (bands of fibrous tissue that connects bone to bone or cartilage to bone, supporting or strengthening a joint). A smooth, durable surface (the articular cartilage) on the head of the arm bone, and a thin lining (synovium) allows smooth motion of the shoulder joint. The joint capsule, a thin sheet of fibers that encircles the shoulder joint, allows a wide range of motion yet provides stability of the joint. The capsule is lined by a thin, smooth synovial membrane. The front of the joint capsule is anchored by three glenohumeral ligaments.

The rotator cuff, a structure composed of tendons and associated muscles that holds the ball at the top of the humerus in the glenoid socket, covers the shoulder joint and joint capsule. The rotator cuff provides mobility and strength to the shoulder joint. A sac-like membrane (bursa) between the rotator cuff and the shoulder blade cushions and helps lubricate the motion between these two structures.

The shoulder is an unstable joint easily subject to injury because of its range of motion, and because the ball of the humerus is larger than the glenoid that holds it. To remain stable, the shoulder must be anchored by its muscles, tendons and ligaments. Some shoulder problems arise from the disruption of these soft tissues due to injury or overuse, or underuse of the shoulder. Other problems can arise from degenerative processes.

For example, instability of the shoulder joint refers to situations that occur when one of the shoulder joints moves or is forced out of its normal position. The two basic forms of shoulder instability are subluxations and dislocations. A partial or incomplete dislocation of the shoulder joint (subluxation) means the head of the humerus is partially out of the socket (glenoid). A complete dislocation of the shoulder joint means that the head of the humerus is completely out of the socket. Anterior instability, for example, refers to a type of shoulder dislocation where the shoulder slips forward, meaning that the humerus moved forward and down out of its joint. Anterior instability may occur when the arm is placed in a throwing position Both partial and complete dislocation cause pain and unsteadiness in the shoulder joint. Patients with repeat dislocation usually require surgery.

Bursitis or tendonitis can occur with overuse from repetitive activities, which cause rubbing or squeezing (impingement) of the rotator cuff under the acromion and in the acromioclavicular joint. Partial thickness rotator cuff tears, most often the result of heavy lifting or fails, can be associated with chronic inflammation and the development of spurs on the underside of the acromion or the AC joint. Full thickness rotator cuff tears most often are the result of impingement.

Osteoarthritis and rheumatoid arthritis can cause destruction of the shoulder joint and surrounding tissue and degeneration and tearing of the capsule or rotator cuff. In osteoarthritis, the articular surface of the joint wears thin. Rheumatoid arthritis is associated with chronic inflammation of the synovium lining, which can produce substances that eventually destroy the inner lining of the joint, including the articular surface.

Shoulder replacement is recommended for subjects with painful shoulders and limited motion. The treatment options are either replacement of the head of the humerus or replacement of the entire socket. However, available treatment options are less than adequate in restoring shoulder joint function.

Just as muscles get stronger through use, the density and strength of bone varies with respect to the bone's load history. To ensure proper bone loading and good bone health, accurate implant placement, good bone fit, and restoration of a healthy anatomic position is critical.

The two major factors that contribute to articulation stability are soft tissue tension and radius of curvature of the glenoid. While some constraint is necessary for a stable joint, too much will increase the forces that contribute to glenoid loosing, one of the most significant problems in shoulder replacement. Because different activities require different levels of constraint in different areas of the glenoid, a simple spherical or dual radius surface may provide too much constraint in certain areas. When the joint is over-constrained, the excess forces that resist humeral head translation also increase glenoid loosening forces.

Optimum glenoid constraint may not be able to be achieved with a simple spherical surface. This principal is emphasized by the natural glenoid/labrum combination, which is not spherical and does not provide the same maximum constraint in all translation directions. Referring to FIG. 1, a currently available shoulder prosthesis glenoid component 10 has an articulating surface 12, which is essentially defined by a spherical or dual radius, fully concave geometry. As such, prior art glenoid components do not take into account the differing levels of constraint required for different activities or the varying curvature of the natural glenoid.

Moreover, since currently available glenoid components have fully concave articulating surfaces, as the humeral head translates, the contact point between the head and glenoid will approach the edge of the glenoid. At a certain point, as illustrated in FIG. 2, a load vector 20 being applied to the glenoid component 10 by a humeral head 22 will no longer pass through the glenoid bone 24, but will load the glenoid component 10 in an overhanging manner, significantly increasing loosening tendencies of the glenoid component 10.

Fixation of the glenoid component of a shoulder prosthesis is particularly important to the outcome of total shoulder reconstruction. Bone cement is commonly used to affix the glenoid component to the scapular neck, and pegs or keels are considered essential for fixation of cemented glenoid components. As shown in FIG. 3, a prior art glenoid component 10 is shown being attached to the glenoid bone 24. As illustrated, the glenoid component can have at least one peg 30. The geometry of the peg 30 typically consists of a substantially cylindrical peg body with various recesses 32 or protrusions for cement fixation. The glenoid bone 24 can have holes 36 that corresponded to the pegs. While this type of geometry may provide adequate fixation of the peg 30 within cement 40, it indiscriminately transfers loads to the cement mantle 40 and cement bone interface 42, creating very high stresses at the proximal edge 44 of the cement mantle. Since cement 40 and the cement bone interface 42 are weak in tension, this often results in the cement mantle 40 breaking free from the bone or breaking apart due to local high stresses.

SUMMARY OF THE INVENTIONS

Accordingly, one embodiment of the present inventions comprises a glenoid component that defines a front surface and a back surface generally opposite the front surface. The substantially concave front surface is configured to articulate with a humeral head. At least one peg extends from the back surface of the glenoid component. The peg comprises a proximal portion that extends from the back surface to a first distance along the peg and a distal portion that extends from an end of the proximal portion to a distal end of the peg. The distal portion of the peg has a maximum cross-sectional diameter with respect to a longitudinal axis of the peg that is less than the minimum cross-sectional diameter of the proximal portion.

Another embodiment of the present inventions comprises a method of implanting an implantable shoulder replacement system having a glenoid component, the glenoid component having at least one peg to anchor the glenoid component to a supportive component, the at least one peg comprising a proximal portion and a distal portion that has a generally smaller diameter than the proximal portion. The method comprising drilling at least one hole in the supportive component to correspond to the at least one peg of the glenoid component, inserting the distal portion of the least one peg into a distal portion of the at least one hole; and press fitting the proximal portion of the at least one peg in the proximal portion of the at least one hole.

According to another embodiment, there is provided an orthopedic device including unique bearing and supportive components, as well as methods of making the same, which can be used in an orthopedic joint to provide improved mobility, adherence to the underlying supportive component, and decreased stresses and overhanging forces that contribute to the loosening of the bearing component.

In another embodiment, the bearing component can be a glenoid component that defines an upper articulating surface and a back surface opposite the articulating surface. The articulating surface can be sized and configured to articulate with a humeral head. The back surface can be configured to be disposed against a supportive component. Further, the bearing component can include at least one peg extending from the back surface of the glenoid component. The peg can have proximal and distal portions. The proximal portion can be configured to be fit into a hole of the supportive component. The distal portion can have a different configuration than the proximal portion such that the distal portion is configured to anchor the glenoid component to the supportive component.

The articulating surface of the glenoid component can be substantially concave. Further, the articulating surface of the glenoid component can comprise at least one complex surface. In this regard, the at least one complex surface can be a surface selected from the group consisting of a continuously variable curvature surface, a multi-radii surface (such as having 3 or more radii), and an asymmetric surface. Additionally, the articulating surface of the glenoid component can further comprise at least one peripheral region having a reverse curvature. Thus, the articulating surface can include a central concave surface surrounded at least partially by at least one secondary reverse curvature surfaces. The back surface of the glenoid component can be substantially convex.

In accordance with another embodiment, the proximal portion of the peg can define a proximal diameter and the distal portion of the peg can define at least one distal diameter. The proximal diameter can be different from the at least one distal diameter. For example, the distal diameter can be smaller than the proximal diameter. Further, the distal portion of the peg can be tapered in shape. The distal portion of the peg can incorporate at least one attachment structure. The attachment structure can be, for example, a radial groove, an annular groove, a linear groove, an axial groove, a step, a flute, radial holes, annular holes, and/or linear holes.

In some embodiments, the proximal portion of the at least one peg can define a proximal diameter and a proximal portion of the hole of the supportive component can define a hole diameter. In such an embodiment, the proximal diameter of the peg can be sized to facilitate a press-fit of the proximal portion of the peg within the hole.

In other embodiments, the distal portion of the at least one peg can be embedded in a cement mantle in the hole of the supportive component. The distal portion of the at least one peg can also be configured to lock into a hollow distal component inserted into the hole in the supportive component. In such an embodiment, the hollow distal component can comprise a material coated for bone ingrowth. The material coated for bone ingrowth can be selected from the group consisting of a metallic material and a polymer material. In some embodiments, the metal material can be titanium.

It is also contemplated that the at least one glenoid peg can range from about 3 mm to about 25 mm in length.

Further, the supportive component can be a scapula bone that comprises an inferior region, a central region and a superior region. In such an embodiment, the glenoid component can be fixed to the scapula bone by attaching at least one peg of long length in the inferior region of the scapula bone, by attaching at least one peg of intermediate length in the central region of the scapula bone, and by attaching at least one peg of short length in the superior region of the scapula bone. Further, it is contemplated that the glenoid can include two or more pegs, and that each peg can be placed in one of a superior, middle and inferior quadrant of the glenoid component. In another embodiment, the glenoid component includes only two pegs positioned inferiorly and superiorly.

In addition, a method is also provided for implanting an implantable shoulder replacement system having a glenoid component. As indicated above, the glenoid component can have at least one peg to anchor the glenoid component to a supportive component. The method can comprise the steps of: drilling at least one hole in the supportive component, the at least one hole corresponding to the at least one peg of the glenoid component, the hole comprising a distal portion and a proximal portion, the at least one hole being sized and configured to receive the at least one peg for facilitating the attachment of the glenoid component to the supportive component; inserting the at least one peg of the glenoid component into the hole of the supportive component, the peg comprising a proximal section defining a proximal diameter, the proximal diameter being sized to facilitate a press fit with the proximal portion of the hole; and press fitting the proximal section of the at least one peg into the proximal portion of the at least one hole.

In another embodiment, the method can further comprising the steps of: filling the distal portion of the hole with cement to form a cement mantle; pressurizing the cement in the hole; and embedding the distal portion of the at least one peg in the cement mantle to secure the peg to the supportive component. In this regard, the pressurizing the cement step can include pressurizing the cement with a ram. Further, the cement step can include pressurizing the cement by injecting high pressure cement with a tight fitting cement nozzle.

In accordance with another embodiment, the can further comprising the steps of: inserting a hollow distal component comprising a material for bone ingrowth into the hole; and locking the distal portion peg into the hollow distal component to secure the peg to the supportive component.

Finally, it is contemplated that supportive component can comprise an inferior region, a central region and a superior region, as noted above, and that the method can further comprise the step of fixing the glenoid component to the supportive component by attaching at least one peg of long length to a hole in the inferior region of the supportive component, by attaching at least one peg of intermediate length to a hole in the anterior region of the supportive component, and by attaching at least one peg of short length to a hole in the superior region of the supportive component.

DETAILED DESCRIPTION OF THE PREFERRED EMBODIMENTS

Figure 1:
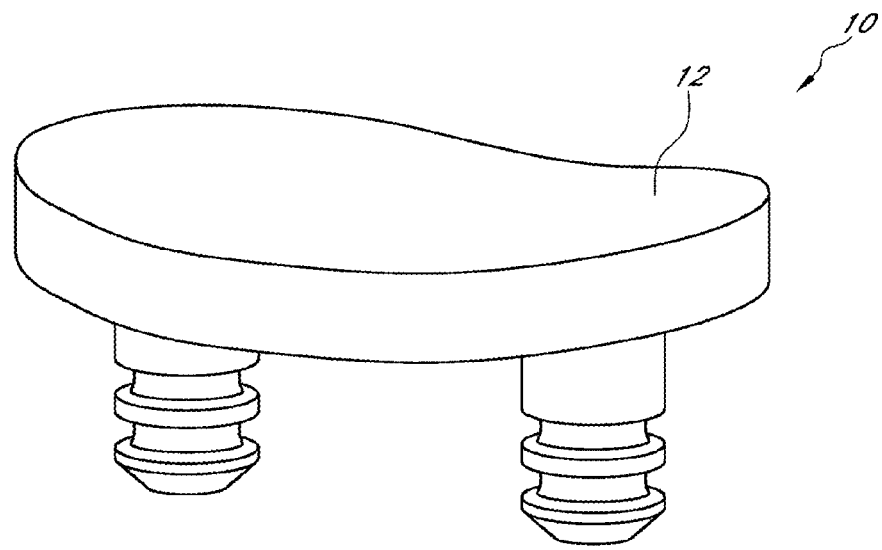
FIG. 1 is a perspective view of a prior art glenoid component with a spherical articulating surface and standard pegs.

In accordance with an embodiment of the present inventions, there is provided unique bearing and supportive components, as well as methods of making the same, which can be used in an orthopedic joint. The bearing and supportive components can provide improved mobility, adherence to the underlying supportive component, and decreased stresses and overhanging forces that contribute to the loosening of the bearing component. In preferred embodiments described herein, the bearing component is utilized as a glenoid component. Further features and other aspects of these components and the joint, as well as disclosure related hereto, are also provided in U.S. Publication No. 2007/0225818, filed on Mar. 21, 2007, entitled "USE OF NON-SPHERICAL ARTICULATING SURFACES IN SHOULDER AND HIP REPLACEMENT," by the Applicants, which claims priority to U.S. Provisional Application No. 60/784,238, filed on Mar. 21, 2006, also entitled "USE OF NON-SPHERICAL ARTICULATING SURFACES IN SHOULDER AND HIP REPLACEMENT," also by the Applicants of the present application, the entire disclosures of each of which are incorporated herein by reference.

As used herein, the term "articulate" means to associate, join, link, or otherwise connect by a joint. An "articulating surface" is a superficial aspect of a first bone at the joint formed by a first bone and a second bone. At the joint, the articulating surface of the first bone associates with the articulating surface of the second bone.

The articulating components of a shoulder replacement system typically comprise of a substantially concave ("bearing") surface that articulates with a substantially convex ("head") surface. The term "convex" as used herein refers to a surface that is curving or bulging outward. The term "concave" as used herein refers to a surface that is curving inward. It is contemplated that a "convex" surface can still include non-convexities, such as concavities or planar areas that deviate from a completely convex surface. Likewise, it is contemplated that a "concave" surface can still include non-concavities, such as convexities or planar areas that deviate from a completely concave surface.

As used herein, the term "constraint" refers to the resistance (meaning any mechanical force that tends to retard or oppose motion) to translation (meaning a uniform movement without rotation) of one body with respect to another. A more complete definition follows below.

Generally, the term "curvature" refers to the amount by which a geometric object deviates from being flat; in the context of an implant, curvature can be compared to a nominal spherical curvature. The term "radius of curvature" refers to the radius of the circle of curvature. Mathematically, it is equal to the absolute value of the reciprocal of the curvature of a curve at a given point.

The term "soft tissue tension" as used herein refers to a measure of the strain in the soft tissue that imparts a force on a body.

The term "subject" as used herein includes animals of mammalian origin, including humans. When referring to animals that typically have one end with a head and mouth, with the opposite end often having the anus and tail, the head end is referred to as the cranial end, while the tail end is referred to as the caudal end. Within the head itself, rostral refers to the direction toward the end of the nose, and caudal is used to refer to the tail direction. The surface or side of an animal's body that is normally oriented upwards, away from the pull of gravity, is the dorsal side; the opposite side, typically the one closest to the ground when walking on all legs, swimming or flying, is the ventral side. On the limbs or other appendages, a point closer to the main body is "proximal;" a point farther away is "distal." This principle shall be followed in relation to embodiments of the apparatuses disclosed herein; a point closer to the main body of the apparatus shall be referred to as "proximal;" a point farther away shall be referred to as "distal."

Three basic reference planes are used in zoological anatomy. A "sagittal" plane divides the body into left and right portions. The "midsagittal" plane is in the midline, i.e. it would pass through midline structures such as the spine, and all other sagittal planes are parallel to it. A "coronal" plane divides the body into dorsal and ventral portions. A "transverse" plane divides the body into cranial and caudal portions.

When referring to humans, the body and its parts are always described using the assumption that the body is standing upright. Portions of the body which are closer to the head end are "superior" (corresponding to cranial in animals), while those farther away are "inferior" (corresponding to caudal in animals). Objects near the front of the body are referred to as "anterior" (corresponding to ventral in animals); those near the rear of the body are referred to as "posterior" (corresponding to dorsal in animals). A transverse, axial, or horizontal plane is an X-Y plane, parallel to the ground, which separates the superior/head from the inferior/feet. A coronal or frontal plane is an Y-Z plane, perpendicular to the ground, which separates the anterior from the posterior. A sagittal plane is an X-Z plane, perpendicular to the ground and to the coronal plane, which separates left from right. The midsagittal plane is the specific sagittal plane that is exactly in the middle of the body.

Structures near the midline are called medial and those near the sides of animals are called lateral. Therefore, medial structures are closer to the midsagittal plane, and lateral structures are further from the midsagittal plane. Structures in the midline of the body are median. For example, the tip of a human subject's nose is in the median line.

Ipsilateral means on the same side, contralateral means on the other side and bilateral means on both sides. Structures that are close to the center of the body are proximal or central, while ones more distant are distal or peripheral. For example, the hands are at the distal end of the arms, while the shoulders are at the proximal ends.

A symmetric subject is assumed when the terms "medial," "lateral," "inferior," "superior," "anterior," and "posterior," are used to refer to an implant.

In accordance with some embodiments disclosed herein, the term "peg" can refer to an elongated structure that protrudes or extends from the back surface of the glenoid. The peg can be cylindrical or otherwise shaped. The peg can be integrally formed with the glenoid or attached thereto. The pegs are protrusions that are typically cemented into prepared holes in the glenoid bone and often have raised or recessed features to mechanically lock to the cement. Some embodiments can be configured with multiple pegs on each glenoid. Optionally, in some embodiments, pegs may be used in combination with a keel.

The term "keel" can refer to a structure that protrudes from the back surface of the glenoid. These protrusions can be cemented into prepared cavities in the glenoid bone and can have raised or recessed features to mechanically lock to the cement. There is typically only one keel on each glenoid, but the keel may be used in combination with pegs.

The term "cement mantle" as used herein can refer to the body of cement between the bone, such as the glenoid bone, and implant.

Figure 4:
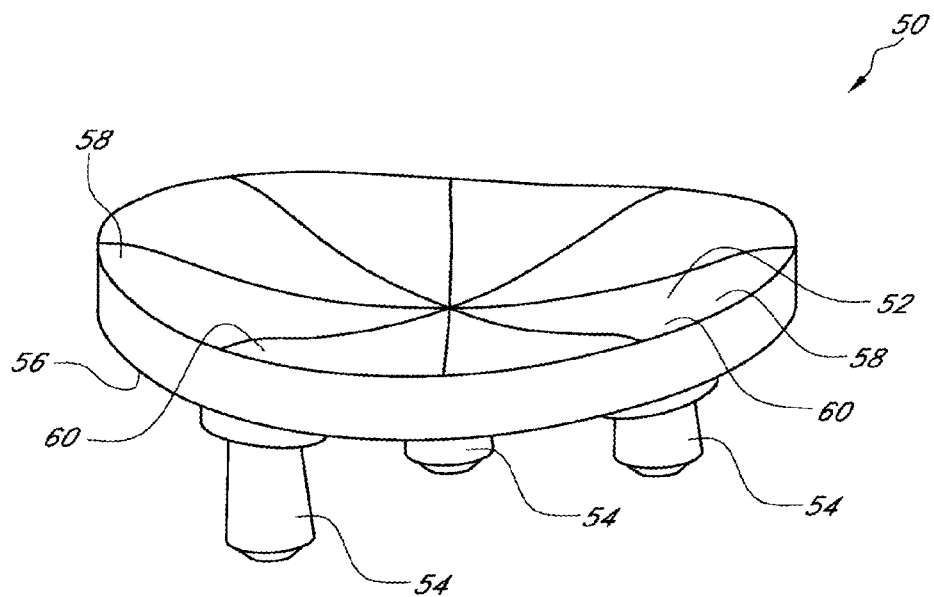
FIG. 4 is a perspective view of a glenoid component having at least one peg, according to an embodiment.

In accordance with an embodiment, a bearing component for orthopedic joint replacement/reconstruction is provided. The bearing component can be, in a preferred embodiment, configured as a glenoid component 50 for use in an orthopedic shoulder prosthesis, as shown in FIG. 4. The glenoid component 50 can define an upper articulating surface 52, which can define a variable curvature in some embodiments. Further, the glenoid component 50 can also include at least one peg 54 extending from a bottom surface 56 of the glenoid component 50. As described further herein, the unique configuration of the articulating surface 52 and the peg 54 can serve to mitigate any loosening of the glenoid 50 during use by reducing unsupported loading, shear forces on the peg, and cement tensile stresses.

Some embodiments can be configured such that the curvature of the articulating surface 52 can vary around a periphery 58 of the glenoid 50. This curvature can be configured to approximate natural constraint levels and reduce the excess forces that cause loosening. For example, as will be described below, the periphery 58 of the glenoid articulating surface 52 can incorporate one or more regions 60 with a "reverse" (radially convex) curvature, which can increase the required amount of humeral head motion in order to cause unsupported loading and in turn reduce loosening.

Figure 2:
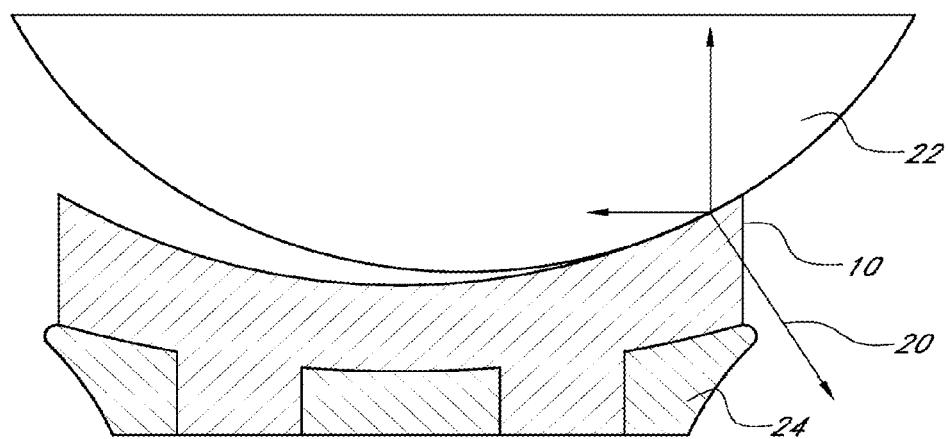
FIG. 2 shows a side cross-sectional view of an illustration of an overhanging load on the prior art glenoid component.
Figure 5:
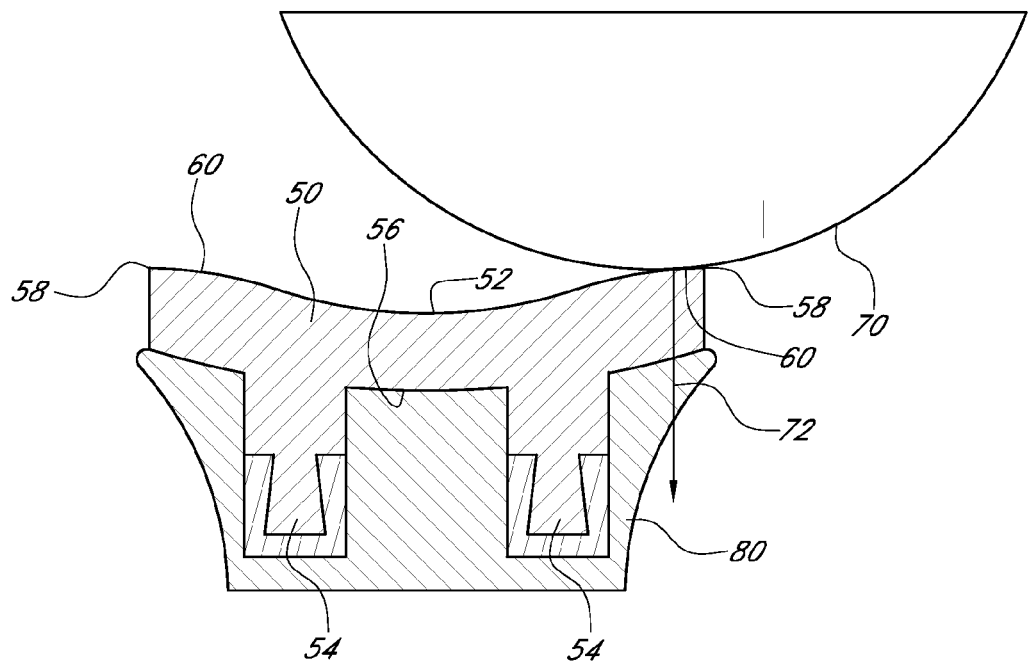
FIG. 5 is a side cross-sectional view of the glenoid component attached to a supportive substrate and further illustrating the effectiveness of a reverse radius of the glenoid component in eliminating overhanging load, according to an embodiment.

FIG. 5 illustrates an embodiment of the present inventions being operative to provide supported loading and reduce loosening of the implant. As shown therein, a humeral head 70 can translate toward the periphery 58 of the glenoid 50, thus causing a load 72 to be transmitted to the glenoid 50 generally about its periphery 58. Additionally, due to the reverse curvature regions 60 adjacent to and/or extending about the periphery 58 of the glenoid 50, the load 72 is transmitted downwardly through substantially all of the glenoid 50 and into a supportive substrate 80. Thus, the load 72 does not extend beyond the back edge of the glenoid, overhanging the glenoid, as in the prior art glenoid 10 illustrated in the loading diagram of FIG. 2.

Figure 3:
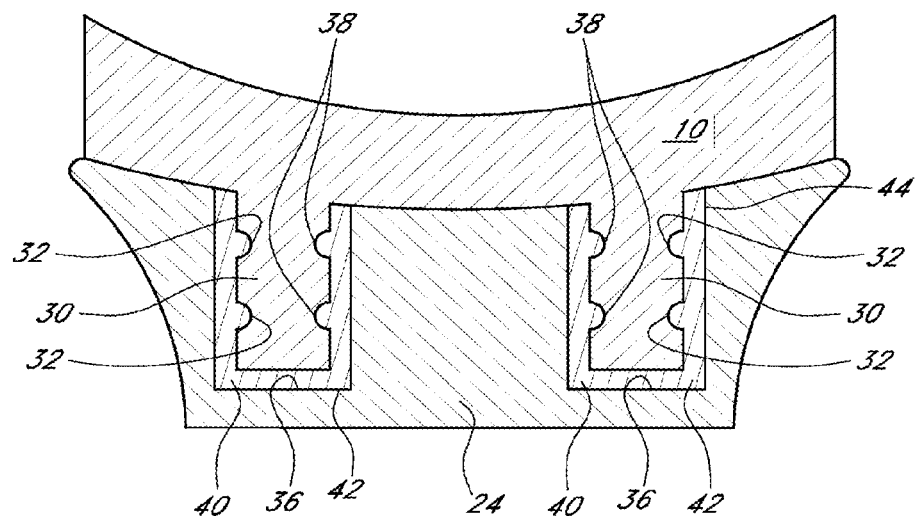
FIG. 3 shows a side cross-sectional view illustrating where high cement stress occurs in the typical cement mantle.
Figure 6:
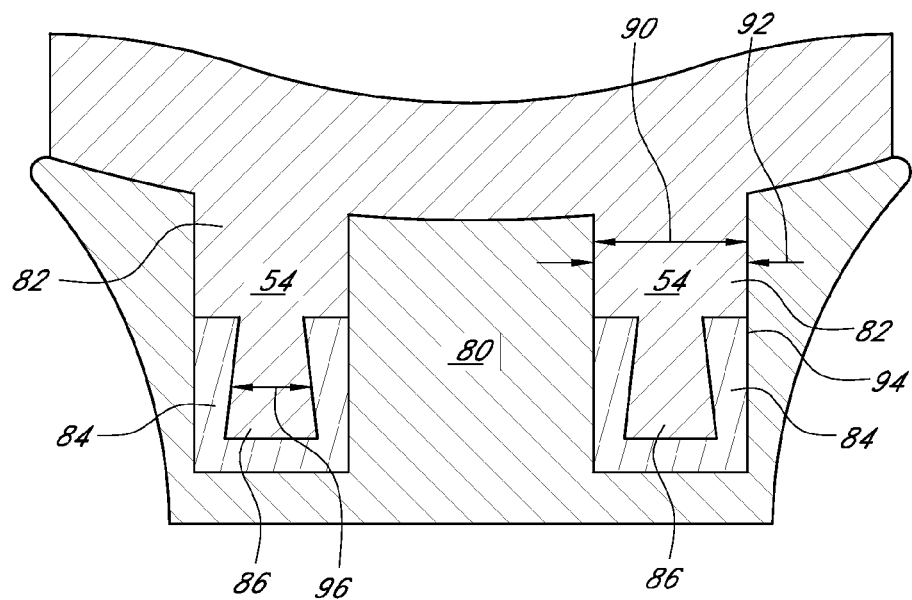
FIG. 6 is a side cross-sectional view illustrating how the glenoid component can reduce tensile stresses in a cement mantle, according to an embodiment.

In accordance with some embodiments, FIG. 6 illustrates that a proximal portion 82 of the glenoid peg 54 can be configured to use a proximal press fit with the glenoid bone or supportive substrate 80 and a cement mantle 84 that is confined to a distal portion 86 of the peg 54. As used herein, the term "proximal press fit" can refer to a tight fit where a diameter 90 of the proximal portion 82 of the peg 54 in a free state may be slightly larger than a diameter 92 of a hole 94 of the supportive substrate 80, the same as the diameter 92 of the hole 94, or slightly smaller than the diameter 92 of the hole 94. In accordance with some embodiments, as illustrated in FIG. 6, the cement mantle 84 is located distally substantially only along the distal portion 86 of the peg 54, which can significantly reduce the peak tensile stresses within the cement mantle 84 compared to the prior art (as illustrated in FIG. 3) and reduces the likeliness of cement failure.

Further, it is contemplated that the distal portion 86 of the peg 54 can be tapered. For example, the cross-sectional area of the distal portion 86 of the peg 54 can increase distally. Further, in embodiments where the peg 54 has a circular cross section, the taper of the distal portion 86 can be such that a distal peg diameter 96 increases distally. The term "taper" can refer to a convex shape that narrows toward a point. This shape will not only mechanically lock the peg 54 in the cement 84, but the shape can apply a more evenly distributed load to the cement mantle 84 than a peg fixation. Therefore, the shape of the distal portion 86 of the peg 54 can be cylindrical or conical; however, the maximum distal diameter 96 should be smaller than or equal to the proximal diameter 90 to facilitate insertion into the hole 94 and allowance for a cement mantle 84.

Figure 7:
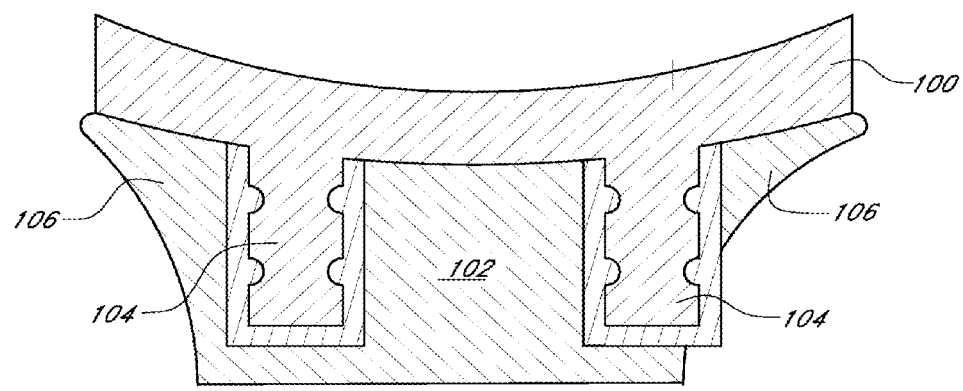
FIG. 7 is a side cross-sectional view of a prior art glenoid component and how a scapula bone can be perforated during drilling if a peg of the glenoid component is too long.

Referring now to FIG. 7, a prior art glenoid component 100 is shown as being attached to a glenoid bone or supportive substrate 102. As illustrated, such a glenoid component 100 can include pegs 104 or keels in a symmetric location with respect to the glenoid component 100. This often can lead to placement of a peg 104 in a location that will not fit within the envelope of the glenoid bone 102. For example, it is very common for a long peg 104 to be placed in a superior area 106 of the bone 102, where the glenoid bone stock is very shallow. This can lead to perforation of the bone 102 while drilling for the peg 104.

Unlike the prior art, all of the pegs of embodiments described herein are preferably positioned such that they are placed in an area of usual substantial bone stock and are of a size and length that reflect the typical depth of the glenoid bone. For example, as illustrated in the embodiment shown in FIG. 8A, the size, length, and configuration of the pegs 54', 54", and 54''' on the bottom surface 56 of the glenoid component 50 can vary depending on the available area and configuration of the glenoid bone or supportive substrate. Accordingly then, the pegs 54', 54", and 54''' will not be embedded in shallow bone stock or cause the glenoid bone to be perforated during preparation for implantation.

Figure 8A:
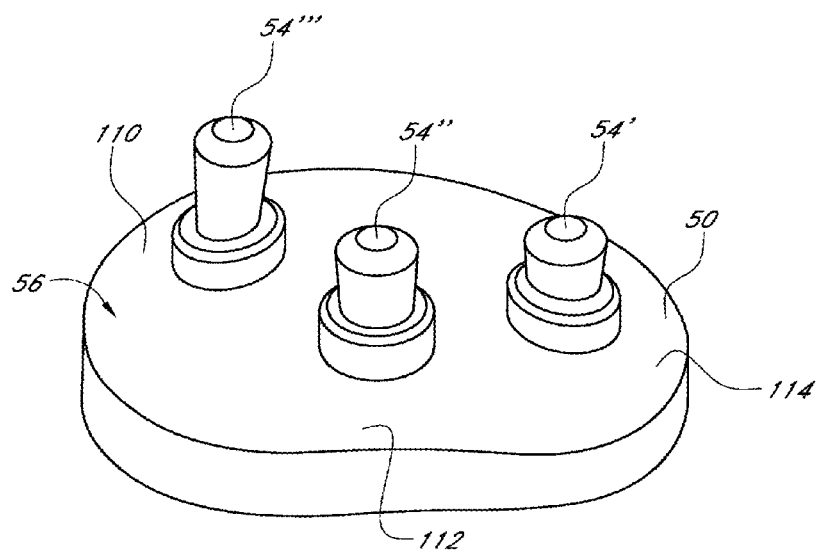
FIG. 8A is a perspective view of an embodiment of a back surface of the glenoid component illustrating placement and size of the pegs.

Therefore, the pegs 54', 54", and 54''', as well as their placement on the bottom surface 56 of the glenoid component 50, can be specifically sized and configured to minimize the potential of scapula perforation and to maximize the structural bone stock to which the pegs adhere. In this regard, the superior glenoid bone is typically very shallow, requiring a shorter peg 54', while the inferior glenoid is much deeper, allowing a longer peg 54'''. It is understood that preferably no peg is to be placed in any area that would risk perforating the scapula during hole preparation. Anticipated regions for peg placement are in the superior, central, and inferior regions of the scapula. Accordingly, as illustrated in FIG. 8A, the bottom surface 56 of the glenoid 50 can comprise an inferior region 110, a central region 112, and a superior region 114. In some embodiments, lengths of the pegs 54', 54", and 54''' can range from about 3 mm to about 20 mm in length. The longest pegs 54''' can therefore be positioned in the inferior region 110, the intermediate lengths 54" can be used in the central region 112, and the shortest lengths 54' can be used in the superior region 114 of the glenoid 50. In other embodiments, the glenoid component only includes two pegs.

Figure 8B:
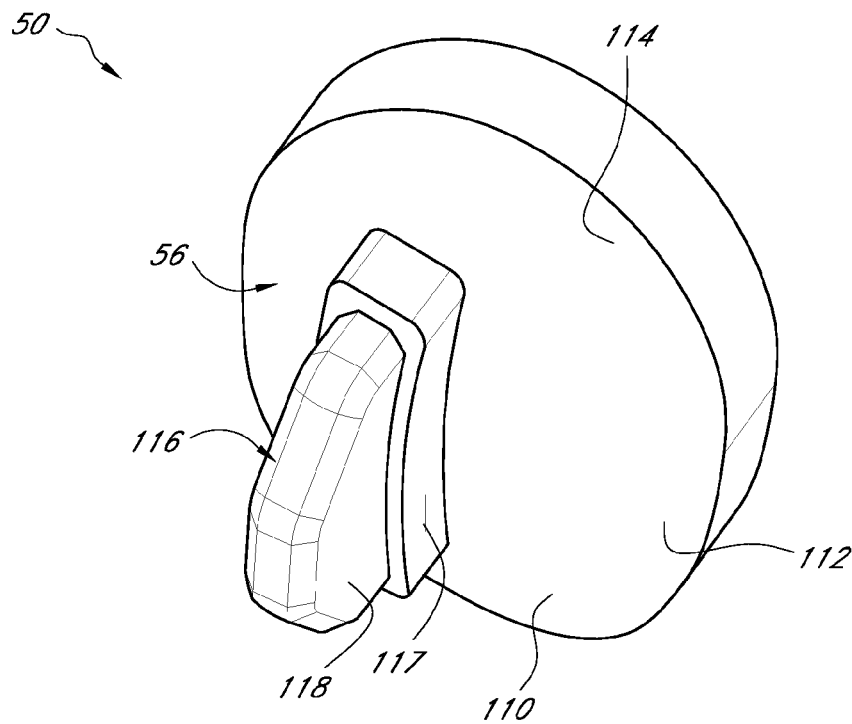
FIG. 8B is a perspective view of another embodiment of a back surface of the glenoid component illustrating placement and size of a keel.
Figure 8C:
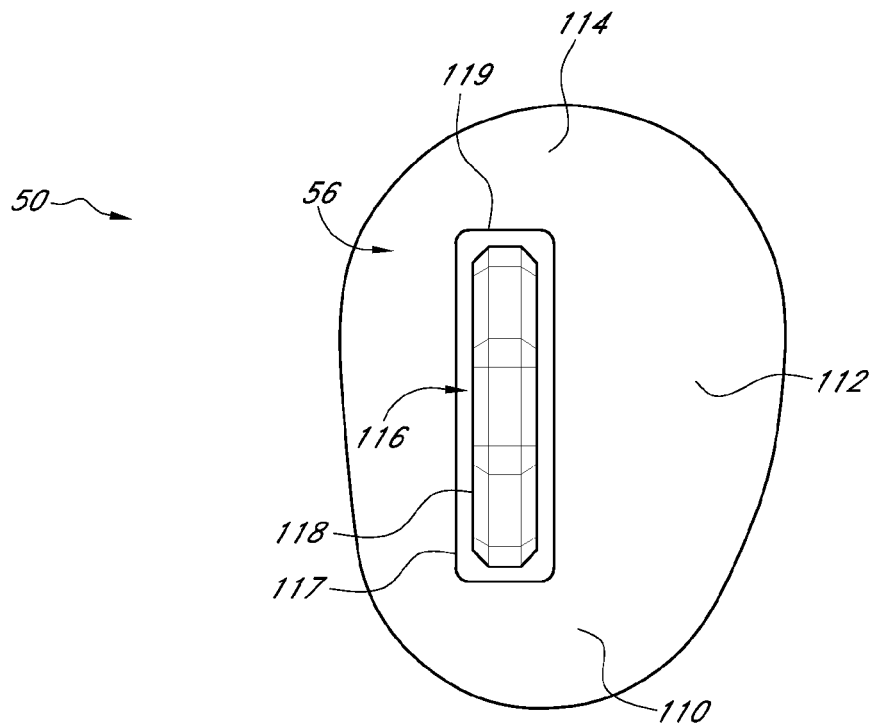
FIG. 8C is a bottom view of the glenoid component shown in FIG. 8B.

With reference to FIGS. 8B and 8C, another embodiment of the glenoid component 50 is illustrated. As shown in the perspective view of FIG. 8B, the glenoid component 50 can be configured to include a keel 116 extending therefrom. The keel 116 can be variously shaped and dimensioned, and can be connected to and extend along the bottom surface 56 intermediate the inferior region 110 and the superior region 114. In some embodiments, the keel 116 can be formed with the glenoid component 50 from a continuous piece of material. However, in other embodiments, the keel 116 can be formed separately from the glenoid component 50 and attached thereto in a later step.

In some embodiments, the keel 116 can be used as an effective alternative to the pegs 54, illustrated in other embodiments herein. Accordingly, the glenoid bone or supportive substrate should be sized and configured to receive the keel 116. It is also contemplated that the keel 116 can be used in concert with the pegs, and that various such embodiments can be formed using the teachings herein.

Accordingly, in some embodiments, such as that shown in FIGS. 8B-C, a proximal portion 117 of the keel 116 can be sized and configured such that it can have a proximal press fit with the glenoid bone or supportive substrate and a cement mantle that can be confined to a distal portion 118 of the keel 116, as similarly noted above with respect to the peg 54. As used herein, the term "proximal press fit" can refer to a tight fit where a periphery 119 of the proximal portion 117 of the keel 116 in a free state may be slightly larger than, the same as, or slightly smaller than a periphery (not shown) of a hole of a supportive substrate into which the keel 116 is inserted. In accordance with some embodiments, the cement mantle can be located distally substantially only along the distal portion 118 of the keel 116, which can significantly reduce the peak tensile stresses within the cement mantle compared to the prior art (as illustrated in FIG. 3) and reduces the likeliness of cement failure.

In addition, as shown in FIG. 8C, the keel 116 can be located off-center along the bottom surface 56 of the glenoid component 50. In this regard, although the illustrated embodiment includes the keel 116 as being substantially parallel with respect to a centerline of the glenoid component 50, and off-center with respect to the centerline, the keel 116 can be oriented transversely with respect to the centerline; further, as discussed above, the keel 116 can have any of a variety of shapes for aiding in the attachment of the keel 116 to the substrate. In this regard, the keel 116 can incorporate any variety of surface textures, geometries, and the like. Thus, the substantially flat and rounded shape of the keel 116 as shown in FIGS. 8B-8C should not be construed as limiting, but merely as a potential embodiment of the keel 116. It is contemplated that modifications to the design and placement of the keel will be apparent given the present disclosure and with skill in the art.

As with the pegs described above, the keel 116 preferably has a proximal portion that has a larger width than the distal portion of the keel 116. In this manner, the keel 116 can be used to used to form a proximal press fit with the glenoid bone or supportive substrate 80 and a cement mantle 84 that is confined to a distal portion of the keel.

With continued reference to FIG. 8C, the outer periphery of the glenoid component 50 can have a shape that is asymmetric with respect to the coronal plane. In addition, this shape can be configured to reduce overhang with the supporting bone by having the periphery generally correspond to the shape of the bone. Accordingly, in one embodiment, the glenoid component has an asymmetric outer periphery configured to increase or maximize converge while reducing overhang. This configuration can be used in combination with the other embodiments described herein.

Figure 9:
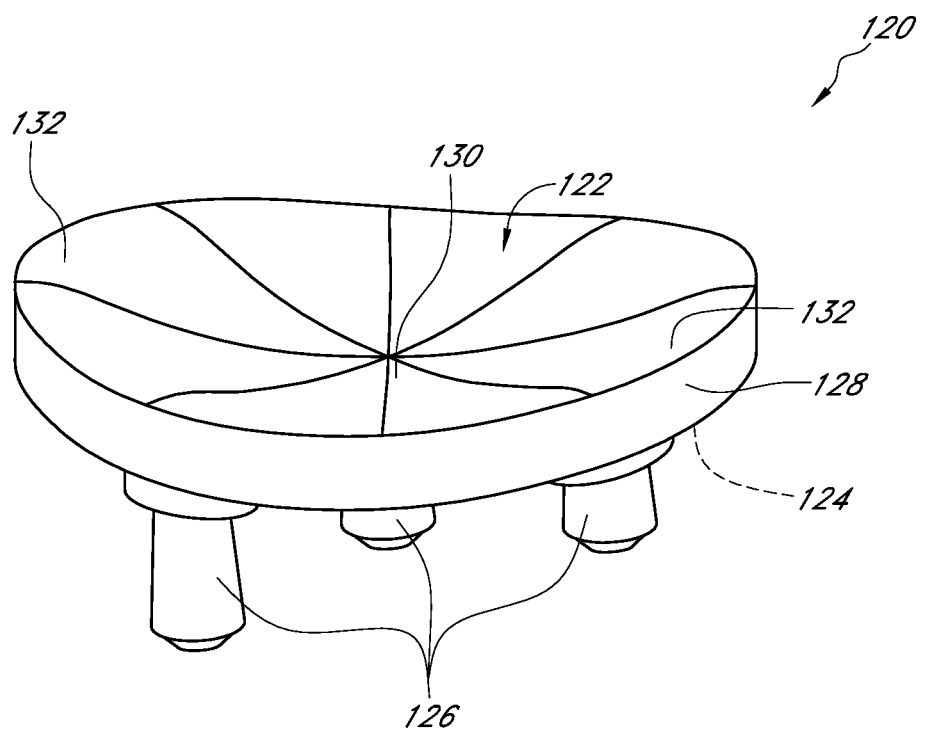
FIG. 9 is a perspective view of another embodiment of the glenoid component.

FIG. 9 is a perspective view of another embodiment of a glenoid component 120, which utilizes several of the features described above. The glenoid component 120 can comprise an upper articulating surface 122, a bottom or back surface 124, and at least one peg 126 extending from the back surface 124. The upper articulating surface 122 can be configured to be substantially concave and in use, can contact a humeral head (not shown). Further, as mentioned above, the term "substantially concave" as used herein refers to a surface that is concave to a great extent or degree. Local convexities can exist, but most of the edge or preferably substantially all of the edge will be higher than the lowest spot, and the slope will not become negative with respect to the sagittal plane. The back surface 124 can be configured to be convex and to rest on a reamed glenoid bone or supportive substrate (not shown). In the art, "reaming" can refer to a process whereby a hole or other shape, such as surfaces such as a sphere or other concave or convex surfaces, is enlarged to an accurate size in order to facilitate implantation of a prosthetic device. The peg(s) 126 can be integrally formed with a body 128 of the glenoid component 120. The peg 126 can extend from the back surface 124 such that it can extend into the glenoid bone and cement mantle during implantation.

In some embodiments, the articulating surface can be substantially concave and comprise a central, concave surface 130 surrounded by one or more secondary reverse curvature surfaces 132 whose cross sections can have a convex curvature in at least one direction, as shown in FIG. 9 and as described above with respect to FIGS. 4 and 5. Both the central and secondary surfaces 130, 132 can be simple, such as a spherical surface, or complex in nature. Examples of complex surfaces include, but are not limited to, surfaces with continuously variable curvature, multi-radius surfaces and asymmetric surfaces. In particular, it is contemplated that the multi-radius surfaces can incorporate three or more radii. The term "continuously variable curvature" as used herein can refer to a curve or surface that does not have abrupt changes in instantaneous radius. Examples of this type of curve include, but are not limited to, certain sinusoidal curves, polynomial curves and spline curves. Continuously variable surfaces can be created by revolving, sweeping, or blending these curves, but can also be created directly from equations. The term "multi-radii surfaces" as used herein refers to a surface that has abrupt changes in instantaneous radius. Such surfaces can be constructed by revolving, sweeping, or blending multi-radii curves and are a simple way to approximate continuously variable curvature. The more radii that are used in these curves, the closer they will be to a continuously variable surface. The term "asymmetric surfaces" as used herein can refer to a surface that is not symmetric about a particular plane, in the case of the glenoid, a plane parallel to the coronal plane. The concave surfaces may be varied to approximate local constraint levels of the natural glenoid and labrum.

Figure 10A:
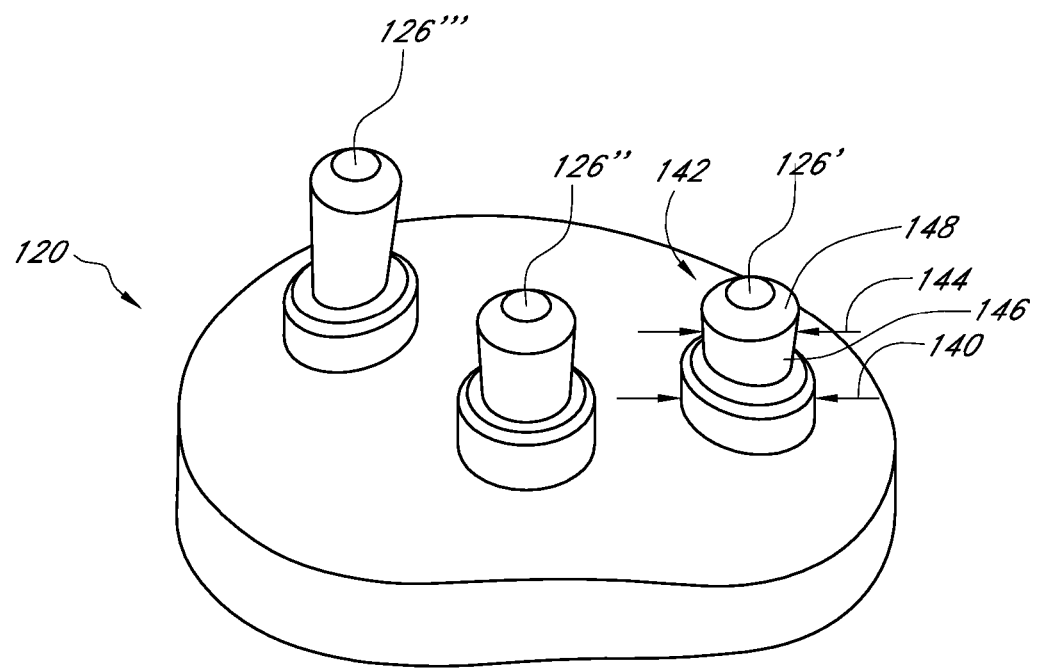
FIG. 10A is a perspective view of a back surface of the glenoid component illustrating placement and size of the pegs, according to yet another embodiment.
Figure 10B:
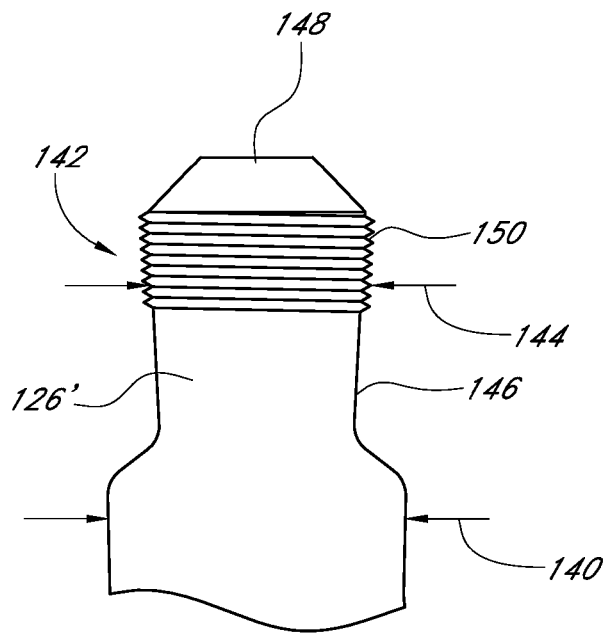
FIG. 10B is a side cross-sectional view of a peg having an attachment structure, according to another embodiment.

Referring now to FIGS. 10A-B, the bottom side of the glenoid 120 of FIG. 9 described above is shown with pegs 126', 126", and 126''' that can be configured as described above with respect to FIGS. 6 and 8. As mentioned above with respect to FIGS. 6 and 8, the pegs 126', 126", and 126''' of some embodiments can have a proximal diameter 140 that can be configured to allow the pegs 126', 126", and 126''' to be press fit into a corresponding hole of a glenoid bone or supportive substrate. Further, the pegs 126', 126", and 126''' can also include a distal section 142 that can, in some embodiments, be tapered or cylindrical.

For example, as shown in FIGS. 10A-B, the distal section 142 can define an effective diameter 144 and be tapered such that the effective diameter 144 decreases from a proximal end 146 toward a distal end 148 of the peg 126', 126", and 126'''. In some embodiments, the effective diameter 144 at the distal end 148 can incorporate an attachment structure 150, such as radial, annular or linear grooves or holes to integrate with the cement. As used herein, the term "groove" refers to an elongated channel, the term "radial" refers to a branching out in all directions from a common center; and the term "annular" refers to being shaped like a ring. Therefore, although FIG. 10B illustrates that the attachment structure 150 is a series of circumferentially extending grooves, the grooves can be configured to extend axially or otherwise along the surface of the peg 126'. In embodiments where the distal portion 148 of the peg 126', 126", and 126''' is conical, such that the diameter 144 increases distally (a "reverse taper"), the attachment structures 150 such as grooves, slots, or holes may not be necessary to provide fixation within the cement. This is beneficial in that the peg can be free to deform within a cement mantle, imparting more evenly distributed loads. Such modifications to the embodiments disclosed herein are contemplated and can be varied given the teachings herein.

According to some preferred embodiments, the glenoid articulating surface can be designed to duplicate anatomic constraint levels of the natural glenoid and labrum. Although functional constraint is also impacted by soft tissue tension, glenoid rim height, and conformity with the humeral head radius, these parameters can all be independently varied. Some of the embodiments disclosed herein address only constraint due to reaction force angle.

Figure 11:
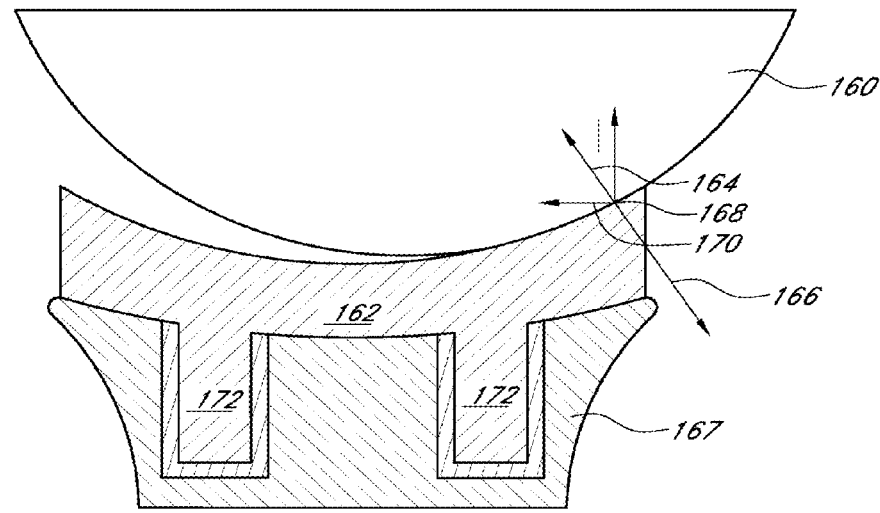
FIG. 11 is a side cross-sectional view of a glenoid component attached to a supportive component and illustrating how reaction force resists translation of a head component, according to another embodiment.

For this purpose, as illustrated in FIG. 11, constraint can be considered a measure of the glenoid's resistance to translation of the humeral head and a function of the cosine of the angle of the reaction force at the point of contact. As shown in FIG. 11, as a head 160 translates along a prior art concave glenoid component 162, a reaction force 164 is transmitted from the glenoid 162 upwardly to the head 160. As appreciated by one of skill, the reaction force 164 is equal and opposite to the normal force 166 applied to the glenoid 162. The normal force 166 passes outwardly from the glenoid 162 and does not pass through the glenoid bone or supportive substrate 167. In this illustration, the constraint can be represented as the cosine of the angle of the reaction force 164 at a point of contact 168. In other words, constraint can be visualized as related to an x-vector 170 of the reaction force 164. Increasing the constraint means that the glenoid fixation features 172 must resist a higher load as well, making it more likely that these features 172 will loosen over time. In order to achieve an appropriate level of constraint, but not needlessly increase the loosening forces, embodiments of the present inventions can utilize complex, variable curvature surfaces to approximate natural constraint levels, as well as to accommodate desired motion.

For example, an aspect of at least one of the embodiments disclosed herein includes the realization that more constraint is required in the inferior area of the glenoid than the anterior area. Using a single or simple curvature, as in the prior art, would also increase the constraint anteriorly, unnecessarily increasing loosening forces and restricting motion. However, as disclosed in embodiments described herein, by varying the level of constraint over the articulating surface of the glenoid to approximate natural constraint levels, the forces that must be resisted by the fixation features are minimized in areas where less constraint is needed.

Figure 12:
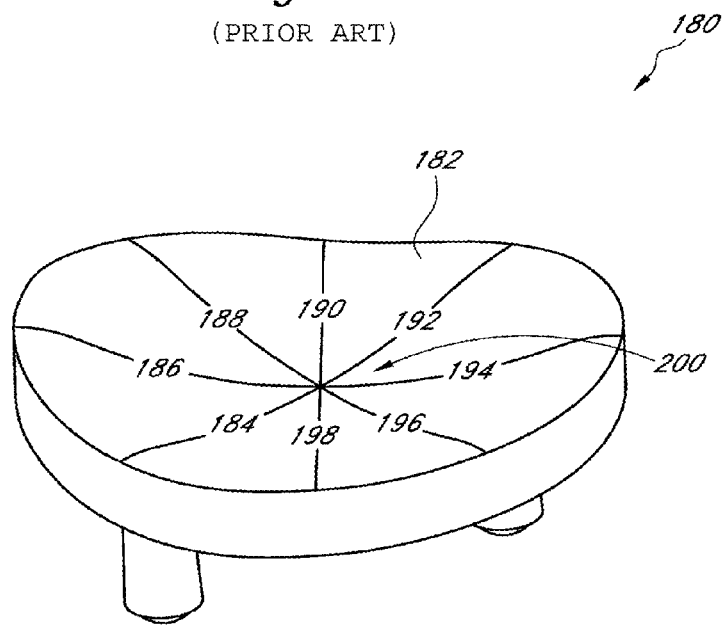
FIG. 12 is a perspective view of an embodiment of the glenoid component illustrating constraint regions, articulating surface geometry, and reverse radius.
Figure 13:
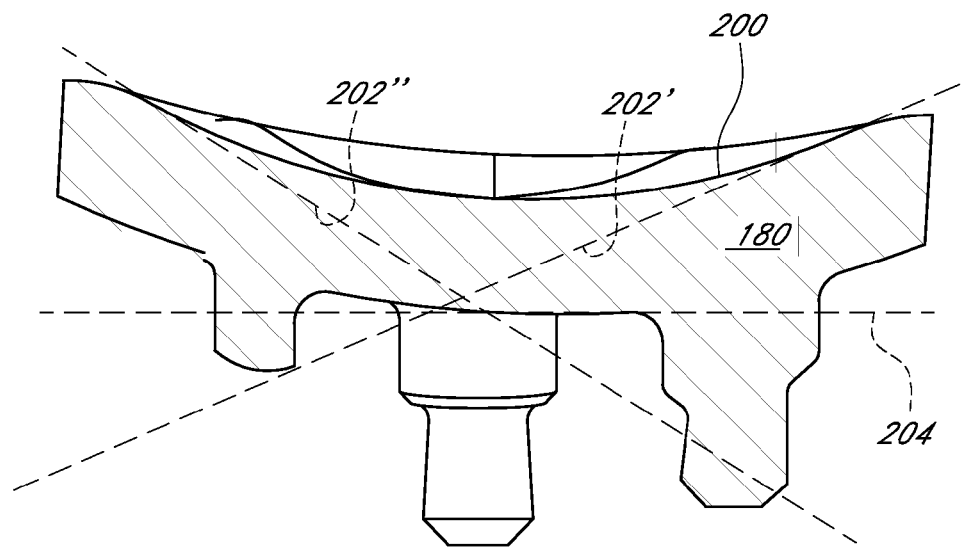
FIG. 13 is a side cross-sectional view of a glenoid component illustrating how the articulating surface can vary in slope and max constraint.

Accordingly, in order to create this geometry, FIG. 12 illustrates an exemplary glenoid 180 having a glenoid surface 182 that is divided into eight areas: inferior-posterior 184, inferior 186, inferior-anterior 188, anterior 190, superior-anterior 192, superior 194, superior-posterior 196, and posterior 198, in which the lines illustrated in FIG. 12 pass through the approximate centers of each area. The slope (and therefore the constraint level) at the edge of a central concave surface 200 can be adjusted to achieve a natural level of constraint in each of the above areas. For example, values obtained from literature, such as: A. M. Halder, S. G. Kuhl, M. E. Zobitz, D. Larson & K. N. An, *Effects of the glenoid labrum and glenohumeral abduction on stability of the shoulder joint through concavity-compression: An in Vitro Study*, THE JOURNAL OF BONE AND JOINT SURGERY AMERICA, 83:1062-1069, 1002, can be utilized to determine the necessary slope(s) of the areas of the central concave area 200. In some embodiments, as shown in cross-sectional side view of FIG. 13, a slope (represented by dashed lines 202', 202") of the concave surface 200 relative to a horizontal plane 204 can represent the maximum effective reaction force constraint. The glenoid surface 182 can be made by blending the curvature in one area to that of its adjacent areas in order to create a single surface with smooth transitions from one area to the next. The slope levels can be changed to within any desired range that facilitates the approximation of a natural and/or required level of constraint. For example, in preferred embodiments, the slope levels can be in the range of about 0 degrees to about 50 degrees.

As illustrated in FIG. 11, as the contact point 168 between the humeral head 160 and the glenoid 162 approaches the edge of the central concave surface, the normal force 166 applied to the glenoid 162 passes beyond the supported back surface of the glenoid 162 and does not pass through the glenoid bone or supportive substrate 167. In this manner, an overhanging load is created. As mentioned above, this situation significantly increases the loosening forces on the glenoid 162 due in part to the symmetric geometry of the upper surface of the prior art glenoid 162 and in part to the completely concave shape of the upper surface of the glenoid 162.

Figure 14:
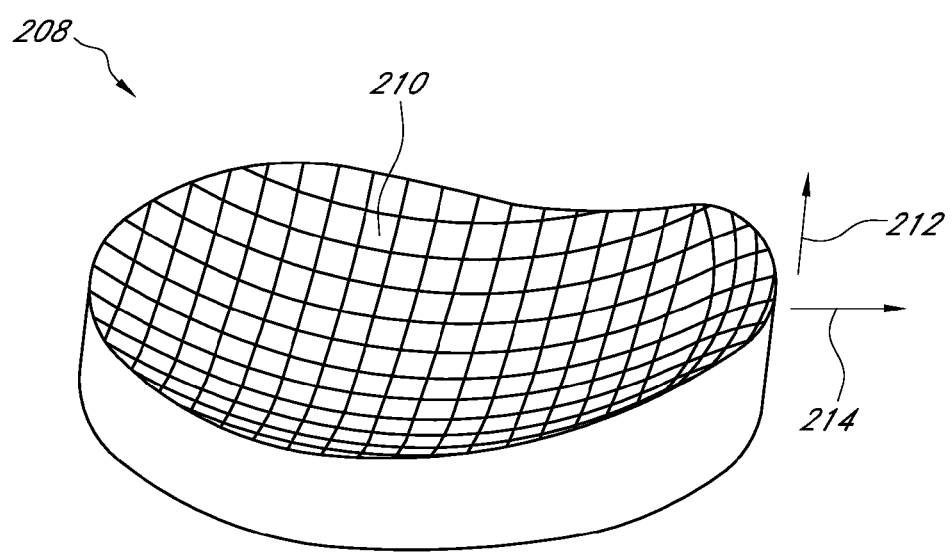
FIG. 14 is a perspective view of an embodiment of the glenoid component wherein the articulating surface thereof is configured to have a directional reverse radius.

In contrast, as shown in FIG. 5, embodiments of the present inventions can be configured such that the convex curvature regions 60 of the articulating surface 52 redirect this force 72 through the glenoid bone or supportive substrate 80 in order to eliminate and/or reduce the severity of overhanging load. Further, such a configuration can allow further translation of the humeral head 70 before an overhanging load or edge load occurs. In some embodiments, this type of reverse curvature can be placed around the entire periphery 58 of the glenoid 50, either evenly or in varying degrees to accommodate anticipated motion differences; in other embodiments, this type of reverse curvature may occur only in certain areas where it is considered necessary. Generally, the radius and width of the reverse curvature should be such that the reverse curvature does not detrimentally increase the stresses in the glenoid component. In some embodiments, the general shape of the reverse curvature may be a non-direction, meaning it is applied without regard to curvature in the normal direction. In other embodiments, a glenoid 208 can have an upper articulating surface 210 that can, as illustrated in FIG. 14, have a uniquely shaped reverse curvature that is concave in a first direction 212, but convex in the normal direction 214 in order to reduce stress.

Figure 15:
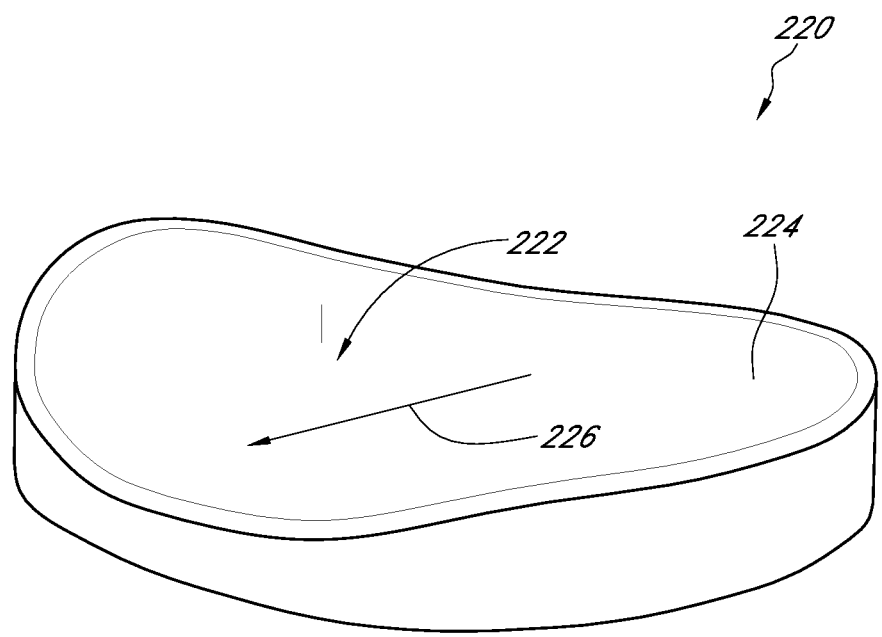
FIG. 15 is a perspective view of an embodiment of the glenoid component illustrating a contoured pathway in the articulating surface.

The embodiments of the articulating surface described above can be created by using complex, non spherical, surfaces to approximate the constraint levels of a natural glenoid with labrum. In other embodiments, complex surfaces also can be used to encourage or discourage a particular type of motion, such as anterior-superior translation. For example, as shown in FIG. 15, it is possible to create a glenoid 220 having a contoured pathway 222 in its upper articulating surface 224. The contoured pathway 222 can be configured as a directional path 226 that allows motion along the pathway 222, but discourages motion normal to the pathway 222. In some embodiments, the contoured pathway 222 can therefore be configured as a smooth surface or area in which the desired translation can occur. Additionally, the contoured pathway 222 can also include eminences, such as a tuberosity or protuberance, in areas where motion is to be discouraged. Such eminences can be formed by steadily or sharply increasing the slope of such areas, or by forming the surface 224 to include protrusions or tubercles, as mentioned. Similarly in other embodiments, a complex surface, such as a continuously variable or multi-radius surface, can be used to optimize stress at a certain point on the glenoid 220 either because higher loads are anticipated in that area or because it is expected to articulate with a particular area on the humeral head with a varying curvature.

Figure 16:
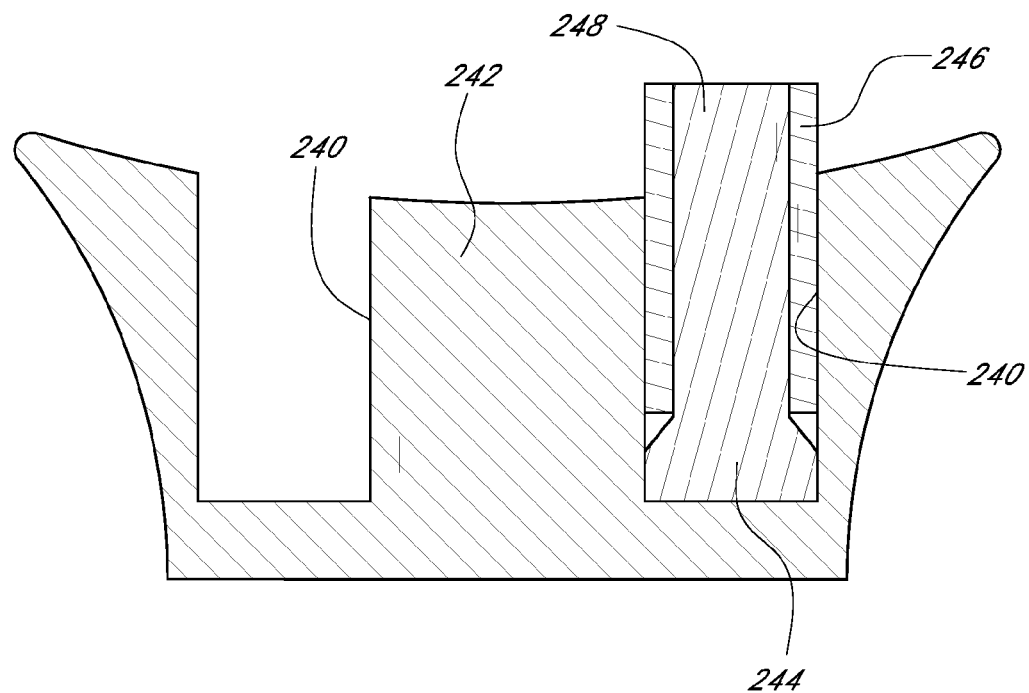
FIG. 16 is a side cross-sectional view of a supportive component and a cement nozzle operative to partially fill holes of the supportive substrate, according to another embodiment.
Figure 17:
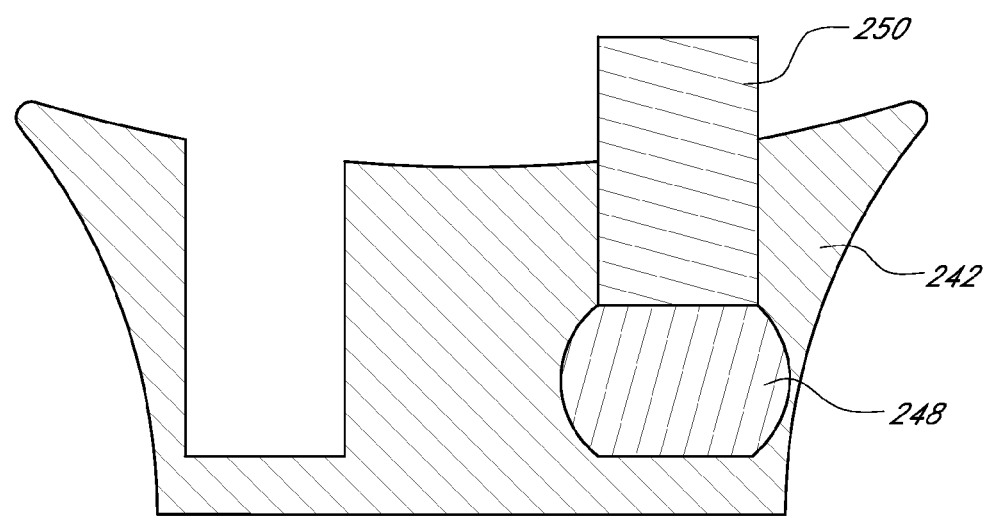
FIG. 17 is a side cross-sectional view of the supportive component of FIG. 16 illustrating a pressurization ram being used to force cement interdigitation with the supportive component, according to another embodiment.

Typically, the glenoid component is fixed by fully cementing the pegs. When a peg is fully cemented, and a shear force is applied to that peg, the peg transfers that load though the cement mantle, creating an uneven mix of dangerously high stresses in the cement near the back surface of the glenoid. These stresses can break the cement mantle and the forces transferred to the cement/bone interface can loosen the cement mantle:

Referring now to FIGS. 16-17, according to another embodiment of the present inventions, a single diameter hole 240 can be drilled into a glenoid bone or supportive substrate 242 in order to prepare the cavity for implantation of a peg or a keel (not shown). When a keel is to be implanted, the hole 240 can be in the form of a longitudinal slot or other shape that complements the shape of the keel, as taught above. A distal portion 244 of the hole 240 can be filled with cement 248 using a nozzle 246. As shown in FIG. 17, after the cement 248 is injected, the cement 248 can be pressurized with a ram 250 to allow cement interdigitation of the cement 248 with porous, cancellous bone 242. The ram 250 can therefore be an impact tool used for driving or forcing the cement 248 into the bone. The bone 242 should therefore have an open or latticed or porous structure.

Figure 18:
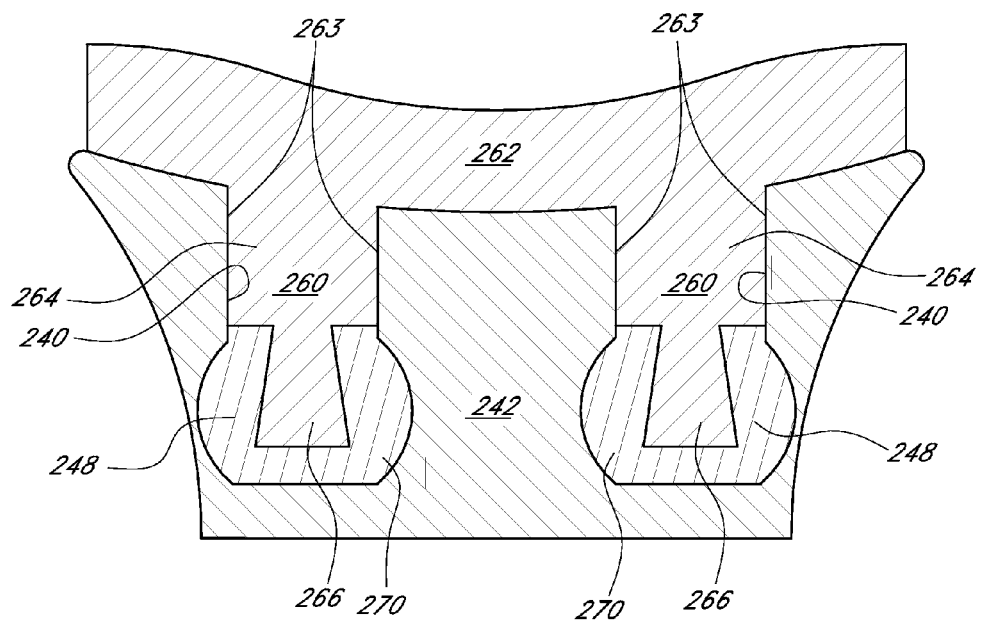
FIG. 18 is a side cross-sectional view of a supportive component illustrating a press-fit placement of pegs of the glenoid component in the holes of the supportive component, according to another embodiment.

As shown in FIG. 18, a peg 260 of a glenoid component 262 can then be inserted into the hole 240. As discussed above, in some embodiments, a larger proximal diameter of the glenoid pegs 260 or the periphery of the keel (not shown) can be press fit directly into the hole 240 or slot without any cement 248 in an interface 263 between the bone 242 and proximal peg 264 or proximal portion of the keel, when used. As the peg 260 or keel is inserted into the hole 240 or slot, the press fit will keep the cement 248 from flowing up the sides of the hole 240 or slot and will pressurize the cement 248 to ensure that it fills in around distal portions 266 of the peg 260 or keel, such as tapered portions, grooves, or any other recessed distal fixation features. It is contemplated that the press fit area will tend to resist shear loads at the bone/peg interface 263, reducing the high tensile stresses at the end of a traditional cement mantle, and the shear forces on the cement mantle, in turn reducing the occurrence of cement fracture or loosening. In some embodiments, in addition to improving shear load carrying properties, because there is no cement mantle about the proximal end 264 of the peg 260 or keel, the risk of seating the glenoid 262 back on a portion of excess, protruding cement is virtually eliminated in the event that the glenoid 262 is partially lifted from the bone 242. Finally, the cement 248 required for a distal mantle 270 is significantly less than for a full cement mantle, increasing the amount of healthy bone preserved and reducing osteonecrosis. As noted, a keel(s) can be used instead of or in addition to the pegs described above. Therefore, each of the above-described advantages and features can be attained in embodiments utilizing a keel(s).

The above-described cement pressurization method can use a ram 250 to force interdigitation of the cement 248 with the bone 242. In other embodiments, interdigitation of the cement with the bone can be accomplished by injecting high pressure cement 248 with a tight fitting cement nozzle.

Figure 19:
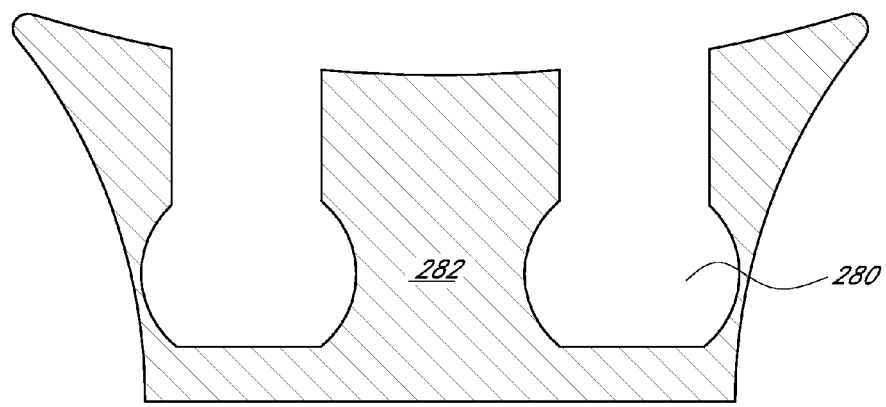
FIG. 19 is a side cross-sectional view of a supportive component illustrating enlarged distal portions of the holes thereof for injecting and creating a cement "anchor," according to yet another embodiment.

In other embodiments, as illustrated in FIG. 19, a larger distal cavity 280 can be prepared in the bone 282 to create a larger cement mantle than the hole diameter. This would tend to create more mechanical retention of the cement within the cavity 280.

In other embodiments, a hollow distal component comprising a material coated for bone ingrowth can be used instead of cement to provide fixation to the bone. The material can be a metallic or polymeric material. Coating materials useful for this purpose can be devised and implemented by a person of ordinary skill in the art. In one embodiment, the material is titanium. The hollow distal component can be inserted into the prepared hole, and each glenoid peg can then lock into or be attached directly to the component.

Thus far, embodiments have been described wherein peg geometry includes two effective diameters. In other embodiments however, a similar effect can be accomplished using multiple diameters, such as tapers, grooves, and otherwise. The important aspect of the multiple diameters is that the proximal diameter can be press fit, while some or all of the distal diameters can be embedded in the cement, the hollow distal component, or otherwise attached to within the hole cavity. Similarly, although a preferred distal geometry is a taper, other embodiments can utilize any of a number of features including, but not limited to, annular grooves, slots, axial grooves, and steps (meaning multiple cylindrical diameters arranged to provide a mechanical interlock with the cement), that could be used instead of, or in combination with, the taper for distal fixation within the cement mantle. Additionally, flutes (meaning a shallow concave groove on the shaft of a column) may be added to the taper to facilitate flow of cement around the taper.

While the present inventions have been described with reference to the specific embodiments thereof, it should be understood by those skilled in the art that various changes may be made and equivalents may be substituted without departing from the true spirit and scope of the inventions. In addition, many modifications may be made to adopt a particular situation, material, composition of matter, process, process step or steps, to the objective spirit and scope of the present inventions. All such modifications are intended to be within the scope of the claims appended hereto.

For example, all of the features described herein are mutually exclusive and can be used in any combination or sub-combination either together or independently from one another.

Where a range of values is provided, it is understood that each intervening value, to the tenth of the unit of the lower limit unless the context clearly dictates otherwise, between the upper and lower limit of that range and any other stated or intervening value in that stated range is encompassed within the inventions. The upper and lower limits of these smaller ranges which may independently be included in the smaller ranges is also encompassed within the inventions, subject to any specifically excluded limit in the stated range. Where the stated range includes one or both of the limits, ranges excluding either both of those included limits are also included in the inventions.

Unless defined otherwise, all technical and scientific terms used herein have the same meaning as commonly understood by one of ordinary skill in the art to which these inventions belong. Although any methods and materials similar or equivalent to those described herein can also be used in the practice or testing of the present inventions, the preferred methods and materials are now described. All publications mentioned herein are incorporated herein by reference to disclose and described the methods and/or materials in connection with which the publications are cited.

The publications discussed herein are provided solely for their disclosure prior to the filing date of the present application. Nothing herein is to be construed as an admission that the present inventions are not entitled to antedate such publication by virtue of prior invention. Further, the dates of publication provided may be different from the actual publication dates which may need to be independently confirmed.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

What is claimed is:

1. An orthopedic device for implantation in a supportive substrate of a scapula prepared with at least one hole, the orthopedic device comprising:
    a glenoid component including a front articulating surface adapted to articulate with a humeral head, and a back surface adapted to engage with the supportive substrate; and
    at least one peg extending from the back surface of the glenoid component, the peg comprising:
        a proximal portion extending from the back surface along a longitudinal axis of the peg, the proximal portion comprising a maximum cross-sectional diameter adapted to provide a proximal press fit with a proximal portion of the hole in the supportive substrate of the scapula; and
        a distal portion extending from the proximal portion, the distal portion comprising a maximum cross-sectional diameter with respect to the longitudinal axis of the peg that is less than the maximum cross-sectional diameter of the proximal portion such that the proximal portion is adapted to help ensure cement fills around the distal portion of the peg, wherein the distal portion tapers such that a cross-section of the distal portion increases distally.

2. The orthopedic device of claim 1 wherein the front surface of the glenoid component comprises at least one complex surface.

3. The orthopedic device of claim 2 wherein the at least one complex surface is a surface selected from the group consisting of a continuously variable curvature surface, a multi-radii surface, and an asymmetric surface.

4. The orthopedic device of claim 1 comprising a reverse curvature in a peripheral region of the glenoid component that transmits a load applied to a peripheral region by the humeral head downwardly through substantially all of the glenoid component and into the supportive substrate.

5. The orthopedic device of claim 1 comprising a reverse curvature in a peripheral region of the glenoid component that directs a load applied to a peripheral region by the humeral head through the back surface of the glenoid component and into the supportive substrate.

6. The orthopedic device of claim 1 comprising a reverse curvature in a peripheral region of the glenoid component that directs a load applied to a peripheral region by the humeral head to the supportive substrate engaged with the back surface of the glenoid component.

7. The orthopedic device of claim 1 comprising a reverse curvature in a peripheral region of the glenoid component that substantially eliminates overhanging loads.

8. The orthopedic device of claim 1 wherein the front surface of the glenoid component comprises at least one contoured pathway configured to direct motion of the humeral head along a directional path.

9. The orthopedic device of claim 1 wherein the front surface of the glenoid component comprises at least one eminence where motion of the humeral head along the front surface is discouraged.

10. The orthopedic device of claim 1 wherein the proximal portion of the peg is substantially cylindrical.

11. The orthopedic device of claim 1 wherein the at least one peg ranges from about 3 mm to about 20 mm in length.

12. The orthopedic device of claim 1 comprising at least three pegs configured asymmetrically on the back surface to engage with inferior, central, and superior regions respectively of the scapula.

13. The orthopedic device of claim 1 wherein the at least one peg comprises:
    a first peg of a first length positioned to engage an inferior region of the scapula;
    a second peg of a second length less than the first length positioned to engage with a central region of the scapula;
    a third peg of a third length less than the second length positioned to engage with a superior region of the scapula.

14. The orthopedic device of claim 1 wherein the at least one peg comprises:
    a first peg configured to engage an inferior region of the scapula; and
    a second peg configured to engage with a superior region of the scapula.

15. The orthopedic device of claim 1 further comprising at least one attachment structure located on the distal portion adapted to mechanically interlock with a cement mantle located in a distal portion of the hole in the supportive substrate of the scapula.

16. The orthopedic device of claim 15 wherein the cement mantle is located substantially along only the distal portion of the peg.

17. The orthopedic device of claim 15 wherein the cement mantle experiences significantly reduced peak tensile stresses compared to a cement mantle extending the length of the peg.

18. The orthopedic device of claim 15 wherein the cement mantle is interdigitated with the supportive substrate.

19. The orthopedic device of claim 15 wherein the attachment structure is selected from the group comprising at least one of a radial groove, an annular groove, a linear groove, an axial groove, a step, a flute, radial holes, annular holes, and linear holes.

20. An orthopedic device for implantation in a supportive substrate of a scapula prepared with at least one hole, the orthopedic device comprising:
    a glenoid component including a front articulating surface adapted to articulate with a humeral head, a back surface adapted to engage with the supportive substrate, and at least three pegs arranged asymmetrically on the back surface of the glenoid component, the three pegs including:

a first peg of a first length positioned to engage with an inferior region of the scapula;

a second peg of a second length less than the first length positioned to engage with a central region of the scapula;

a third peg of a third length less than the second length positioned to engage with a superior region of the scapula;

wherein each of the first, second and third peg has a proximal portion and a distal portion having a first cross-sectional diameter and a second cross-sectional diameter, respectively, wherein the first cross-sectional diameter is spaced from the back surface at a distance less than a distance the second cross-sectional diameter is spaced from the back surface, and wherein the second cross-sectional diameter is substantially less than the first cross-sectional diameter; and a plurality of cement mantles for securing the glenoid component to the supportive substrate including a first, a second, and a third cement mantle each located substantially only along the distal portions of each of the first, second, and third pegs, respectively, and secured to the distal portions of each of the first, second, and third pegs, respectively.

* * * * *

UNITED STATES PATENT AND TRADEMARK OFFICE
CERTIFICATE OF CORRECTION

PATENT NO. : 9,474,619 B2
APPLICATION NO. : 11/689424
DATED : October 25, 2016
INVENTOR(S) : Leo M. Reubelt and Peter L. Verrillo It is certified that error appears in the above-identified patent and that said Letters Patent is hereby corrected as shown below:

On the Title Page

At Item (56), Page 3, Column 2, Line 55, change "prosthese" to --prosthesis--.

At Item (56), Page 3, Column 2, Line 66, change "Fractrures,"" to --Fractures,"--.

In the Specification

At Column 1, Line 9, change "2007," to --2006,--.

At Column 15, Line 8, change "mantle:" to --mantle.--.

Signed and Sealed this
Twenty-seventh Day of February, 2018

Andrei Iancu
*Director of the United States Patent and Trademark Office*